US012018282B2

United States Patent
Nakamura et al.

(10) Patent No.: US 12,018,282 B2
(45) Date of Patent: Jun. 25, 2024

(54) METHOD FOR PRODUCING INSULIN-PRODUCING CELL FROM MESENCHYMAL STEM CELL, INSULIN-PRODUCING CELL, CELL STRUCTURE, AND PHARMACEUTICAL COMPOSITION

(71) Applicants: FUJIFILM Corporation, Tokyo (JP); Tokushima University, Tokushima (JP)

(72) Inventors: Kentaro Nakamura, Ashigarakami-gun (JP); Mitsuo Shimada, Tokushima (JP); Tetsuya Ikemoto, Tokushima (JP)

(73) Assignees: FUJIFILM Corporation, Tokyo (JP); TOKUSHIMA UNIVERSITY, Tokushima (JP)

( * ) Notice: Subject to any disclaimer, the term of this patent is extended or adjusted under 35 U.S.C. 154(b) by 632 days.

(21) Appl. No.: 16/870,388

(22) Filed: May 8, 2020

(65) Prior Publication Data
US 2020/0392464 A1 Dec. 17, 2020

Related U.S. Application Data

(63) Continuation of application No. PCT/JP2018/041639, filed on Nov. 9, 2018.

(30) Foreign Application Priority Data

Nov. 10, 2017 (JP) .................................. 2017-216927

(51) Int. Cl.
 *C12N 5/00* (2006.01)
 *C12N 5/071* (2010.01)

(52) U.S. Cl.
CPC ........ *C12N 5/0676* (2013.01); *C12N 2500/38* (2013.01); *C12N 2501/12* (2013.01); *C12N 2501/16* (2013.01); *C12N 2501/335* (2013.01); *C12N 2506/1384* (2013.01)

(58) Field of Classification Search
CPC ........ C12N 2506/1346; C12N 2500/38; C12N 2501/12; C12N 2501/335
See application file for complete search history.

(56) References Cited

U.S. PATENT DOCUMENTS

| | | | |
|---|---|---|---|
| 2007/0020242 A1* | 1/2007 | Ramiya | C12N 5/0676 435/366 |
| 2012/0101040 A1* | 4/2012 | Ogiwara | A61P 9/10 514/13.3 |
| 2012/0329157 A1 | 12/2012 | Nakamura | |
| 2017/0203005 A1* | 7/2017 | Iwazawa | A61K 9/16 |

FOREIGN PATENT DOCUMENTS

| | | |
|---|---|---|
| CN | 101570741 A | 11/2009 |
| CN | 102242146 | * 11/2011 |
| CN | 102858381 A | 1/2013 |
| CN | 105062953 A | 11/2015 |
| WO | WO 2009/116087 A1 | 9/2009 |
| WO | WO 2016/052504 A1 | 4/2016 |

OTHER PUBLICATIONS

European Communication pursuant to Article 94(3) EPC for European Application No. 18876691.9, dated Jul. 8, 2022.
Japanese Office Action for corresponding Japanese Application No. 2019-552399, dated Jan. 5, 2022, with English translation.
Extended European Search Report, dated Oct. 22, 2020, for European Application No. 18876691.9.
Ikemoto et al., "A New 2-Step Acceleration Protocol Using a Histone Deacetylase Inhibitor to Generate Insulin-Producing Cells from Adipose-Derived Mesenchymal Stem Cells," Pancreas, vol. 47, No. 4, Apr. 2018 (Apr. 1, 2018), pp. 477-481, XP055738154.
Ikemoto et al., "In vitro and in vivo Effects of Insulin-Producing Cells Generated by Xeno-antigen Free 3D Culture with RCP Piece," Scientific Reports, vol. 9, No. 1, Published online Jul. 24, 2019, pp. 1-9, XP055738015.

(Continued)

*Primary Examiner* — Gyan Chandra
(74) *Attorney, Agent, or Firm* — Birch, Stewart, Kolasch & Birch, LLP

(57) ABSTRACT

An object of the present invention is to provide a method for producing insulin-producing cells having sufficient glucose responsiveness from mesenchymal stem cells, an insulin-producing cell having sufficient glucose responsiveness, a cell structure containing the insulin-producing cell, and a pharmaceutical composition. According to the present invention, there is provided a method for producing an insulin-producing cell from a mesenchymal stem cell, including (a) a step of producing a cell structure by incubating a plurality of biocompatible macromolecular blocks and a plurality of mesenchymal stem cells, and (b) a step of culturing one or more of the mesenchymal stem cells before the incubation in the step (a), the mesenchymal stem cell in the incubation in the step (a), or the cell structure produced in the step (a) in a medium containing the GLP-1 receptor agonist, and (c) a step of culturing the cell structure obtained in the step (a) or the step (b) in a medium containing the water-soluble vitamin and the hepatocyte growth factor.

15 Claims, 8 Drawing Sheets

Specification includes a Sequence Listing.

(56) References Cited

OTHER PUBLICATIONS

Millman et al., "Autologous Pluripotent Stem Cell-Derived ß-Like Cells for Diabetes Cellular Therapy," Diabetes, vol. 66, No. 5, May 2017 (Apr. 20, 2017), pp. 1111-1120, XP055738176.
Nakamura et al., "Introduction to a New Cell Transplantation Platform via Recombinant Peptide Petaloid Pieces and Its Application to Islet Transplantation with Mesenchymal Stem Cells," Transplant International, vol. 29, No. 9, 2016 (Sep. 1, 2016), pp. 1039-1050, XP055587752.
International Preliminary Report on Patentability and Written Opinion of the international Searching Authority (Forms PCT/IB/326, PCT/IB/373, PCT/ISA/237), dated May 22, 2020, for International Application No. PCT/JP2018/041639, with an English translation.
International Search Report (Form PCT/ISA/210), dated Feb. 5, 2019, for International Application No. PCT/JP2018/041639, with an English translation.
Phuc et al., "Differentiating of banked human umbilical cord blood-derived mesenchymal stem cells into insulin-secreting cells", In Vitro Cell. Dev.Biol.—Animal, vol. 47, 2011 (published online Nov. 17, 2010), pp. 54-63 ( 10 pages).
Shimada et al., "A New 2 Step Protocol for Human Adipose Derived Mesenchymal Stem Cell Differentiation To Insulin-Producing Cells Using Xeno-Antigen Free Reagents", Transplant International, Sep. 2017, vol. 30 (Suppl. 2), pp. 518 (2 pages).
Sun et al., "Differentiation of bone marrow-derived mesenchymal stem cells from diabetic patients into insulin-producing cells in vitro", Chinese Medical Journal, 2007, vol. 120, No. 9, pp. 771-776 ( 6 pages).
"Abstracts of the 18th Congress of the European Society for Organ Transplantation." Transplant International, vol. 30, Suppl. 2, Sep. 2017, p. 518, P465 (2 pages total).
Japanese Office Action for corresponding Japanese Application No. 2019-552399, dated May 11, 2021, with English translation.
Chinese Office Action and Search Report for corresponding Chinese Application No. 201880072674.9, dated Dec. 26, 2022, with English translation.
Chinese Office Action for corresponding Chinese Application No. 201880072674.9, dated Aug. 1, 2023, with an English translation.
Japanese Office Action for corresponding Japanese Application No. 2022-061665, dated May 2, 2023, with English translation.
Chinese Office Action for corresponding Chinese Application No. 201880072674.9, dated Jan. 17, 2024, with an English translation.
European Communication pursuant to Article 94(3) EPC for corresponding European Application No. 18876691.9, dated Jan. 31, 2024.

* cited by examiner

CELL ONLY (VPA−)

CELL ONLY (VPA+)

CELL STRUCTURE (VPA−)

CELL STRUCTURE (VPA+)

METHOD FOR PRODUCING INSULIN-PRODUCING CELL FROM MESENCHYMAL STEM CELL, INSULIN-PRODUCING CELL, CELL STRUCTURE, AND PHARMACEUTICAL COMPOSITION

CROSS-REFERENCE TO RELATED APPLICATIONS

This application is a Continuation of PCT International Application No. PCT/JP2018/041639 filed on Nov. 9, 2018, which claims priority under 35 U.S.C § 119(a) to Japanese Patent Application No. 2017-216927 filed on Nov. 10, 2017. Each of the above application(s) is hereby expressly incorporated by reference, in its entirety, into the present application.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2870-0754PUS1_ST25.txt" created on Aug. 7, 2020 and is 12,307 bytes in size. The sequence listing contained in this .txt file is part of the specification and is hereby incorporated by reference herein in its entirety.

BACKGROUND OF THE INVENTION

1. Field of the Invention

The present invention relates to a method for producing an insulin-producing cell from a mesenchymal stem cell, an insulin-producing cell, a cell structure containing the insulin-producing cell, and a pharmaceutical composition.

2. Description of the Related Art

Several reports have been made on induction of differentiation of insulin-producing cells from mesenchymal stem cells. On the other hand, human-derived cells and other (rat or mouse)-derived cells have completely different properties, and it is known that even if differentiation using cells other than human cells is successfully induced, this does not serve as a reference for induction of differentiation of human-derived cells.

In a case where the reports on the induction of differentiation in human-derived cells are reviewed, for example, in Non-Patent Literature 1, successful induction of differentiation from human umbilical cord-derived mesenchymal stem cells into insulin-expressing cells has been reported. However, in Non-Patent Literature 1, it was not made successful in secretion of insulin up to insulin expression at a gene expression level.

In addition, in Non-Patent Literature 2, induction of differentiation from human bone marrow-derived mesenchymal stem cells into insulin-producing cells is described, and insulin secretion is also confirmed. However, in view of FIG. 4 of Non-Patent Literature 2, it is recognized that a ratio of an amount of insulin secretion when a glucose concentration is 5.56 mmol/L and an amount of insulin secretion when a glucose concentration is 16.7 mmol/L (this is called stimulation index (SI)) is clearly less than 2. As described above, in Non-Patent Literature 2, a practical insulin-producing cell cannot be produced because it does not satisfy SI≥2, which is considered to have glucose responsiveness.

Prior Art Literatures

Non-Patent Literature

Non-Patent Literature 1: In Vitro Cell. Dev. Biol.-Animal (2011) 47: 54-63
Non-Patent Literature 2: Chinese Medical Journal 2007; 120 (9): 771-776

SUMMARY OF THE INVENTION

As described above, there have been several reports on attempts to induce differentiation of mesenchymal stem cells into insulin-secreting cells, but a practical method has not been established, and a new method has been sought. An object of the present invention is to provide a method for producing insulin-producing cells having sufficient glucose responsiveness from mesenchymal stem cells, an insulin-producing cell having sufficient glucose responsiveness, a cell structure containing the insulin-producing cell, and a pharmaceutical composition.

As a result of intensive examination to solve the problem, the present inventors found that it is possible to produce insulin-producing cells having sufficient glucose responsiveness by producing a cell structure by incubating a biocompatible macromolecular block and a mesenchymal stem cell in the presence of a GLP-1 (glucagon-like peptide 1) receptor agonist and culturing the cell structure in a medium containing a water-soluble vitamin and a hepatocyte growth factor, thereby completing the present invention.

That is, according to the present invention, the following inventions are provided.

<1> A method for producing an insulin-producing cell from a mesenchymal stem cell, the method including:
(a) a step of producing a cell structure which contains a plurality of biocompatible macromolecular blocks and a plurality of mesenchymal stem cells and in which at least one of the biocompatible macromolecular block is arranged in a gap between the plurality of mesenchymal stem cells, by incubating the plurality of biocompatible macromolecular blocks and the plurality of mesenchymal stem cells;
(b) a step of culturing one or more of the mesenchymal stem cells before the incubation in the step (a), the mesenchymal stem cell in the incubation in the step (a), or the cell structure produced in the step (a) in a medium containing the GLP-1 receptor agonist; and
(c) a step of culturing the cell structure obtained in the step (a) or the step (b) in a medium containing the water-soluble vitamin and the hepatocyte growth factor.
<2> The method according to <1>, in which the step (b) is performed for 3 to 14 days.
<3> The method according to <1> or <2>, in which the step (c) is performed for 7 to 35 days.
<4> The method according to any one of <1> to <3>, in which the GLP-1 receptor agonist is exendin-4.
<5> The method according to any one of <1> to <4>, in which the water-soluble vitamin is nicotinamide.
<6> The method according to any one of <1> to <5>, in which the medium in the step (b) further contains activin A.
<7> The method according to any one of <1> to <6>, in which the medium in the step (c) further contains a histone deacetylation inhibitor.

<8> The method according to <7>, in which the histone deacetylation inhibitor is a valproic acid.

<9> The method according to any one of <1> to <8>, in which the step (a) and the step (b) are steps of producing a cell structure which contains a plurality of biocompatible macromolecular blocks and a plurality of mesenchymal stem cells and in which at least one of the biocompatible macromolecular blocks is arranged in a gap between the plurality of mesenchymal stem cells, by incubating the plurality of biocompatible macromolecular blocks and the plurality of mesenchymal stem cells in a medium containing a GLP-1 receptor agonist.

<10> The method according to any one of <1> to <9>, in which the mesenchymal stem cells are fat-derived stem cells.

<11> The method according to any one of <1> to <10>, in which a size of one biocompatible macromolecular block is 10 μm to 300 μm.

<12> The method according to any one of <1> to <11>, in which a thickness or a diameter of the cell structure is 150 μm to 3 cm.

<13> The method according to any one of <1> to <12>, in which the biocompatible macromolecular block is formed of a recombinant peptide.

<14> The method according to <11>, in which the recombinant peptide is represented by the following formula. Formula: A-[(Gly-X-Y)$_n$]$_m$-B, in the formula, A represents an arbitrary amino acid or an amino acid sequence, B represents an arbitrary amino acid or an amino acid sequence, n pieces of X each independently represent any amino acid, n pieces of Y each independently represent any amino acid, n represents an integer of 3 to 100, and m represents an integer of 2 to 10. Here, n pieces of Gly-X-Y may be the same as or different from each other.

<15> The method according to <13> or <14>, in which the recombinant peptide is any one of a peptide formed of an amino acid sequence described in SEQ ID NO: 1; a peptide which is formed of an amino acid sequence in which one or several amino acids are deleted, substituted, or added in the amino acid sequence described in SEQ ID NO: 1 and has a biocompatibility; or a peptide which is formed of an amino acid sequence having 85% or more of sequence identity to the amino acid sequence described in SEQ ID NO: 1 and has a biocompatibility.

<16> The method according to any one of <1> to <15>, in which in the biocompatible macromolecular block, a biocompatible macromolecule is cross-linked by heat, ultraviolet rays, or an enzyme.

<17> The method according to any one of <1> to <16>, in which the biocompatible macromolecular block is in a form of granules obtained by grinding a porous body of biocompatible macromolecules.

<18> An insulin-producing cell produced by the method according to any one of <1> to <17>.

<19> The cell according to <18>, in which Stimulation Index, obtained by dividing a concentration of insulin in a medium when the cell structure containing 5×10$^5$ insulin-producing cells was cultured in a 2 mL of Krebs-Ringer bicarbonate buffer at a concentration of 20 mmol/L glucose for 60 minutes with a concentration of insulin in a medium when the cell structure was cultured in a 2 mL of Krebs-Ringer bicarbonate buffer at a concentration of 3 mmol/L glucose for 60 minutes, is 2.5 or more.

<20> A cell structure containing an insulin-producing cell produced by the method according to any one of <1> to <17>.

<21> The cell structure according to <20>, in which Stimulation Index, obtained by dividing a concentration of insulin in a medium when the cell structure containing 5×10$^5$ insulin-producing cells was cultured in a 2 mL of Krebs-Ringer bicarbonate buffer at a concentration of 20 mmol/L glucose for 60 minutes with a concentration of insulin in a medium when the cell structure was cultured in a 2 mL of Krebs-Ringer bicarbonate buffer at a concentration of 3 mmol/L glucose for 60 minutes, is 2.5 or more.

<22> A pharmaceutical composition including the insulin-producing cell according to <18> or <19> or the cell structure according to <20> or <21>.

<23> The pharmaceutical composition according to <22>, wherein the pharmaceutical composition is a therapeutic agent for diabetes.

According to the method of the present invention, it is possible to produce insulin-producing cells having sufficient glucose responsiveness from mesenchymal stem cells. The insulin-producing cell of the present invention and the insulin-producing cell contained in the cell structure of the present invention have sufficient glucose responsiveness.

DESCRIPTION OF THE PREFERRED EMBODIMENTS

Figure 1:
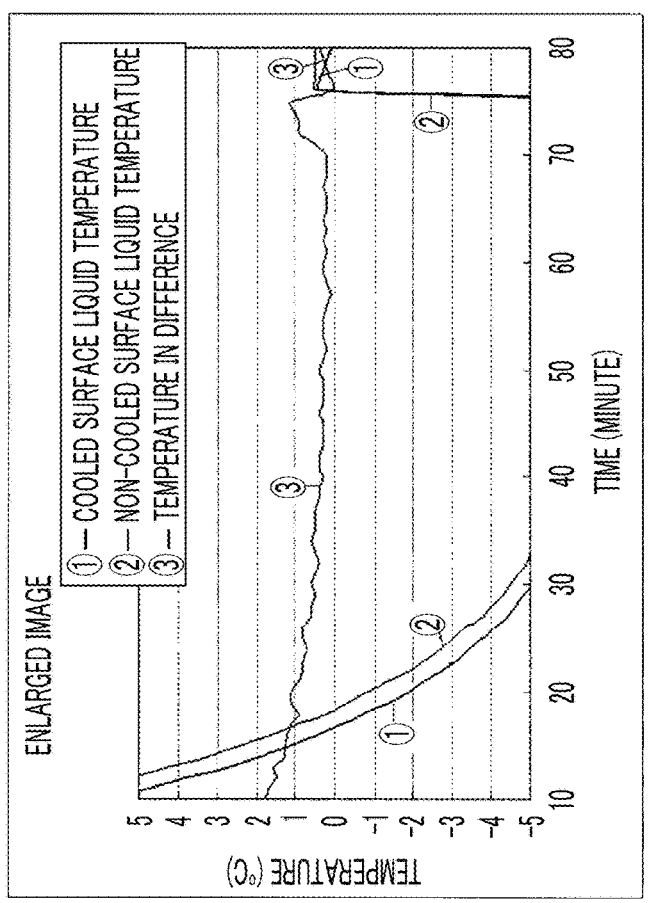
FIG. 1 shows a liquid temperature profiling of an experiment described in Condition A.
Figure 1:
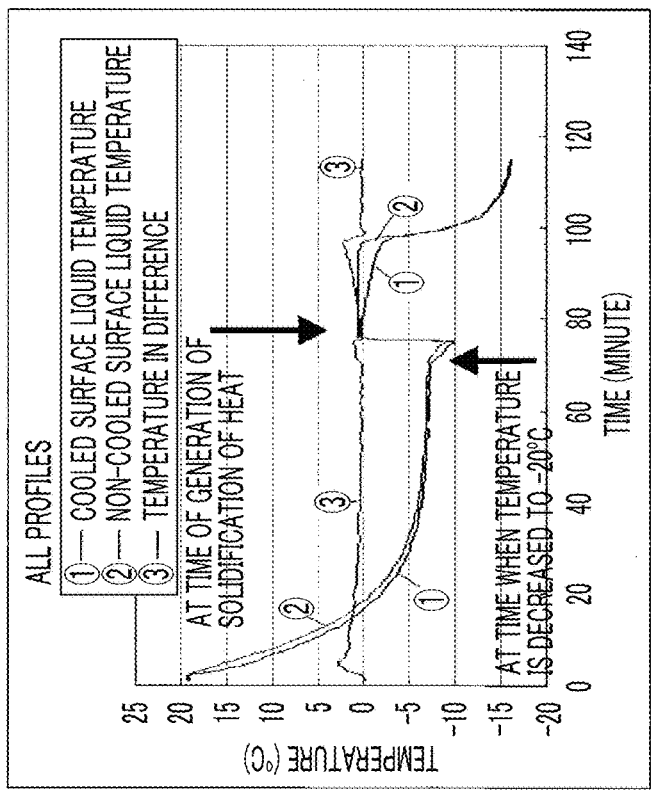

Hereinafter, embodiments for carrying out the present invention will be described in detail.

The cell structure in the present invention is referred to as a mosaic cell aggregation (a cell aggregation having a mosaic shape) in some cases, in the present specification. In addition, "to" in the present specification indicates a range including numerical values described before and after it as a minimum value and a maximum value, respectively.

The present invention relates to a method for producing insulin-producing cells from mesenchymal stem cells, the method including:

(a) a step of producing a cell structure which contains a plurality of biocompatible macromolecular blocks and a plurality of mesenchymal stem cells and in which at least one of the biocompatible macromolecular block is arranged in a gap between the plurality of mesenchymal stem cells, by incubating the plurality of biocompatible macromolecular blocks and the plurality of mesenchymal stem cells;

(b) a step of culturing one or more of the mesenchymal stem cells before the incubation in the step (a), the mesenchymal stem cell in the incubation in the step (a), or the cell structure produced in the step (a) in a medium containing the GLP-1 receptor agonist; and (c) culturing the cell structure obtained in the step (a) or the step (b) in a medium containing a water-soluble vitamin and a hepatocyte growth factor.

[Regarding Step (a)]

The step (a) is a step of producing a cell structure which contains a plurality of biocompatible macromolecular blocks and a plurality of mesenchymal stem cells and in which at least one biocompatible macromolecular block is arranged in a gap between the plurality of mesenchymal stem cells, by incubating a plurality of biocompatible macromolecular blocks and a plurality of mesenchymal stem cells.

(1) Biocompatible Macromolecular Block (1-1) Biocompatible Macromolecules

Biocompatibility means a property which does not cause a significantly harmful response such as a long-term and chronic inflammatory reaction, during contact with a living body. Whether or not the biocompatible macromolecules used in the present invention are decomposed within a living body is not particularly limited as long as the biocompatible macromolecules have affinity to the living body. However, biodegradable macromolecules are preferable. Specific examples of non-biodegradable materials include polytetrafluoroethylene (PTFE), polyurethane, polypropylene, polyester, vinyl chloride, polycarbonate, acryl, stainless steel, titanium, silicone, and 2-methacryloyloxyethyl phosphoryl choline (MPC). Specific examples of the biodegradable materials include naturally derived peptides, polypeptide (for example, gelatin or the like to be described below) such as recombinant peptide or chemically synthesized peptide, polylactic acid, polyglycolic acid, lactic acid-glycolic acid copolymers (PLGA), hyaluronic acid, glycosaminoglycan, proteoglycan, chondroitin, cellulose, agarose, carboxymethyl cellulose, chitin, and chitosan. Among these, a recombinant peptide is particularly preferable. Devising of an improvement of cell adhesion properties in these biocompatible macromolecules may be performed. Specifically, methods such as "coating of the surface of a base material with a cell adhesion substrate (fibronectin, vitronectin, or laminin) or peptides of a cell adhesion sequence (an RGD sequence, an LDV sequence, an REDV (SEQ ID NO: 2) sequence, a YIGSR (SEQ ID NO: 3) sequence, a PDSGR (SEQ ID NO: 4) sequence, an RYVVLPR (SEQ ID NO: 5) sequence, an LGTIPG (SEQ ID NO: 6) sequence, an RNIAEIIKDI (SEQ ID NO: 7) sequence, an IKVAV (SEQ ID NO: 8) sequence, an LRE sequence, a DGEA (SEQ ID NO: 9) sequence, and a HAV sequence, which are represented by one-letter notation of amino acids)", "aminization and cationization of the surface of a base material", or "plasma treatment on the surface of a base material and hydrophilic treatment due to corona discharge" can be used.

The kind of polypeptide containing a recombinant peptide or a chemically synthesized peptide is not particularly limited as long as a polypeptide has biocompatibility. For example, gelatin, collagen, elastin, fibronectin, ProNectin, laminin, tenascin, fibrin, fibroin, entactin, thrombospondin, and RetroNectin (registered trademark) are preferable, and gelatin, collagen, and atelocollagen are most preferable. As the gelatin to be used in the present invention, natural gelatin, recombinant gelatin, or chemically synthesized gelatin is preferable, and recombinant gelatin is more preferable. The natural gelatin referred to herein means gelatin produced using naturally derived collagen.

The chemically synthesized peptide or the chemically synthesized gelatin means an artificially synthesized peptide or gelatin. The synthesis of a peptide such as gelatin may be solid phase synthesis or liquid phase synthesis, but is preferably solid phase synthesis. The solid phase synthesis of a peptide is well-known to those skilled in the art, and examples thereof include a fluorenyl-methoxy-carbonyl group (Fmoc group) synthesis method in which a Fmoc group is used for protection of an amino group, and a tert-butyl oxy carbonyl group (Boc group) synthesis method in which a Boc group is used for protection of an amino group. As a preferred aspect of the chemically synthesized gelatin, it is possible to apply the contents described in Recombinant Gelatin to be described below in the present specification.

A "1/IOB" value which is a hydrophilic value of biocompatible macromolecules used in the present invention is preferably within a range of 0 to 1.0, more preferably within a range of 0 to 0.6, and still more preferably within a range of 0 to 0.4. IOB is an index of hydrophilic and hydrophobic properties based on an organic conceptual diagram representing polarity/non-polarity of an organic compound proposed by Atsushi HUJITA, and the details thereof are described in, for example, Pharmaceutical Bulletin, vol. 2.2, pp. 163-173 (1954), "Area of Chemistry", vol. 11, 10, pp. 719-725 (1957), and "Fragrance Journal", vol. 50, pp. 79-82 (1981). Briefly, the root of every organic compounds is set to methane (CH4), and all of other compounds are regarded as derivatives of methane. Certain numerical values for the number of carbons thereof, a substituent group, a transformation portion, a ring, and the like are set, and an organic value (OV) and an inorganic value (IV) are obtained by adding the score thereof. These values are plotted on a diagram in which the organic value is shown on the X-axis and the inorganic value is shown on the Y-axis. IOB in the organic conceptual diagram refers to a ratio of the inorganic value (IV) to the organic value (OV) in the organic conceptual diagram, that is, "inorganic value (IV)/organic value (OV)". The details of the organic conceptual diagram can be referred to "New Edition Organic Conceptual Diagram-Foundation and Application-" (written by Yoshio KOUDA, Sankyo Shuppan Co., Ltd., 2008). In the present specification, the hydrophilic and hydrophobic properties are represented by a "1/IOB" value which was obtained by taking a reciprocal number of JOB. This is a notation of representing more hydrophilic properties as the "1/IOB" value becomes small (close to 0).

The hydrophilic properties and water absorbency become high by making the "1/IOB" value of the macromolecules used in the present invention be within the range, which effectively acts to hold nutrient components. As a result, it is presumed that this contributes to stabilization and survival of cells in the cell structure (mosaic cell aggregation) according to the present invention.

In a case where the biocompatible macromolecules used in the present invention are polypeptides, the hydrophilic and hydrophobic indexes represented by a grand average of hydropathicity (GRAVY) value are preferably −9.0 to 0.3, and more preferably −7.0 to 0.0. The grand average of the hydropathicity (GRAVY) value can be obtained by methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi 1., Appel R. D., Bairoch A.; ExPASy: the proteomics server for in-depth protein knowledge and analysis.; Nucleic Acids Res. 31:3784-3788 (2003)."

The hydrophilic properties and water absorbency become high by making the GRAVY value of the macromolecules used in the present invention be within the above-described range, which effectively acts to hold nutrient components. As a result, it is presumed that this contributes to stabilization and survival of cells in the cell structure (mosaic cell aggregation) according to the present invention.

(1-2) Cross-Linking

The biocompatible macromolecules used in the present invention may be or may not be cross-linked, but are preferably cross-linked. By using the cross-linked biocompatible macromolecules, it is possible to obtain an effect of preventing instant decomposition during culturing in a medium and during transplantation into a living body. As general cross-linking methods, thermal cross-linking, cross-linking using aldehydes (for example, formaldehyde, glutaraldehyde, or the like), cross-linking using a condensation agent (carbodiimide, cyanamide, or the like), enzymatic cross-linking, photocross-linking, ultraviolet cross-linking, a hydrophobic interaction, hydrogen bonding, an ionic interaction, and the like are known, and it is also possible to use the above-described cross-linking methods in the present invention. As the cross-linking methods used in the present invention, thermal cross-linking, ultraviolet cross-linking, or enzymatic cross-linking is more preferable, and thermal cross-linking is particularly preferable.

In a case of performing cross-linking using an enzyme, there is no particular limitation as long as the enzyme has a cross-linking action between macromolecular materials. However, it is possible to perform cross-linking preferably using transglutaminase or laccase, and most preferably using transglutaminase. Specific examples of protein to be subjected to enzymatic cross-linking using transglutaminase are not particularly limited as long as the protein has a lysine residue and a glutamine residue. The transglutaminase may be derived from a mammal or may be derived from a microorganism. Specific examples include mammal-derived transglutaminase which has been sold as Activa series manufactured by Ajinomoto Co., Inc., and a reagent; guinea pig liver-derived transglutaminase manufactured by, for example, Oriental Yeast Co., Ltd., Upstate USA Inc., or Biodesign International, Inc.; goat-derived transglutaminase; rabbit-derived transglutaminase; and human-derived blood coagulation factors (Factor XIIIa, Haematologic Technologies, Inc.).

The reaction temperature in a case of performing cross-linking (for example, thermal cross-linking) is not particularly limited as long as cross-linking can be performed, but is preferably −100° C. to 500° C., more preferably 0° C. to 300° C., still more preferably 50° C. to 300° C., particularly preferably 100° C. to 250° C., and most preferably 120° C. to 200° C.

(1-3) Recombinant Gelatin

The recombinant gelatin referred in the present invention means polypeptides or protein-like substances which have an amino acid sequence similar to that of gelatin produced through gene recombination technology. The recombinant gelatin which can be used in the present invention preferably has a repetition of a sequence (X and Y each independently represent any amino acids) represented by Gly-X-Y which is characteristic to collagen. Here, a plurality of pieces of Gly-X-Y may be the same as or different from each other. Preferably, two or more sequences of cell adhesion signals are included in one molecule. As the recombinant gelatin used in the present invention, it is possible to use recombinant gelatin having an amino acid sequence derived from a partial amino acid sequence of collagen, and to use recombinant gelatin disclosed in, for example, EP 1014176A2, U.S. Pat. No. 6,992,172B, WO 2004/085473 A, and WO 2008/103041 A. However, the recombinant gelatin is not limited thereto. Preferred recombinant gelatin used in the present invention is recombinant gelatin of the following aspect.

The recombinant gelatin is excellent in biocompatibility with original performance of natural gelatin, and is excellent in non-infection properties since there is no concern of bovine spongiform encephalopathy (BSE) and the recombinant gelatin with not being naturally derived. In addition, the recombinant gelatin is even compared to natural gelatin, and a sequence is determined. Therefore, it is possible to accurately design the strength and degradability so as to reduce deviation through cross-linking or the like.

The molecular weight of recombinant gelatin is not particularly limited, but is preferably 2,000 to 100,000 (2 kDa (kilo dalton) to 100 kDa), more preferably 2,500 to 95,000 (2.5 kDa to 95 kDa), further more preferably 5,000 to 90,000 (5 kDa to 90 kDa), and most preferably 10,000 to 90,000 (10 kDa to 90 kDa).

The recombinant gelatin preferably has a repetition of a sequence represented by Gly-X-Y which is characteristic to collagen. Here, a plurality of pieces of Gly-X-Y may be the same as or different from each other. In Gly-X-Y, Gly represents glycine and X and Y represent an arbitrary amino acid (preferably represents an arbitrary amino acid other than glycine). The sequence represented by Gly-X-Y characteristic to collagen is a partial structure which is extremely specific compared to other proteins in a composition or a sequence of an amino acid of gelatin and collagen. In this section, glycine occupies about one third of the entirety of the amino acid sequence, and one sequence is repeated every three sequences. Glycine is the simplest amino acid. Therefore, there is a little restraint in arrangement of molecular chains and glycine significantly and contributes to regeneration of a helix structure during gelation. It is preferable that amino acids represented by X and Y contain many imino acids (proline and oxyproline) and occupy 10% to 45% of the entirety of the sequence. Preferably 80% or more of the sequence of the amino acids, more preferably 95% or more of the sequence of the amino acids, and most preferably 99% or more of the sequence of the amino acids in the recombinant gelatin has a repeating structure of Gly-X-Y.

In general gelatin, a polar amino acid with an electrical charge and a polar non-charged amino acid exist by 1:1 in polar amino acids. Here, the polar amino acid specifically indicates cysteine, aspartic acid, glutamic acid, histidine, lysine, asparagine, glutamine, serine, threonine, tyrosine, and arginine. Among these, the polar non-charged amino acid indicates cysteine, asparagine, glutamine, serine, threonine, and tyrosine. In recombinant gelatin used in the present invention, the proportion of the polar amino acid in the whole constituent amino acid is 10% to 40% and preferably 20% to 30%. It is preferable that the proportion of a non-charged amino acid in the polar amino acid is equal to or more than 5% and less than 20% and preferably equal to or more than 5% and less than 10%. Furthermore, it is preferable that any one amino acid or preferably two or more amino acids among serine, threonine, asparagine, tyrosine, and cysteine are not contained on a sequence.

In general, in polypeptides, minimum amino acid sequences which work as cell adhesion signals are known (for example, "Pathophysiology", Vol. 9, No. 7 (1990) p. 527 published by Nagai Shoten Co., Ltd.). The recombinant gelatin used in the present invention preferably has two or more these cell adhesion signals in one molecule. As the specific sequences, sequences such as an RGD sequence, an LDV sequence, an REDV (SEQ ID NO: 2) sequence, a YIGSR (SEQ ID NO: 3) sequence, a PDSGR (SEQ ID NO: 4) sequence, an RYVVLPR (SEQ ID NO: 5) sequence, an LGTIPG (SEQ ID NO: 6) sequence, an RNIAEIIKDI (SEQ ID NO: 7) sequence, an IKVAV (SEQ ID NO: 8) sequence, an LRE sequence, a DGEA (SEQ ID NO: 9) sequence, and a HAV sequence, which are represented by one-letter notation of amino acids are preferable in that there are many kinds of cells adhered. An RGD sequence, a YIGSR (SEQ ID NO: 3) sequence, a PDSGR (SEQ ID NO: 4) sequence, an LGTIPG (SEQ ID NO: 6) sequence, an IKVAV (SEQ ID NO: 8) sequence, and a HAV sequence are more preferable and an RGD sequence is particularly preferable. In the RGD sequence, an ERGD (SEQ ID NO: 10) sequence is preferable. It is possible to improve the production amount of substrate of a cell using recombinant gelatin having cell adhesion signals.

As the arrangement of RGD sequences in recombinant gelatin used in the present invention, it is preferable that the number of amino acids between RGDs is between 0 to 100, and the number of amino acids between RGDs is more preferably between 25 to 60 without being even.

The content of this minimum amino acid sequence is preferably 3 to 50, more preferably 4 to 30, particularly preferably 5 to 20, and most preferably 12, in one molecule of protein in view of cell adhesion properties and growth properties.

In recombinant gelatin used in the present invention, the proportion of RGD motifs with respect to the total number of amino acids is preferably at least 0.4%. In a case where recombinant gelatin contains 350 or more amino acids, each stretch of the 350 amino acids preferably contains at least one RGD motif. The proportion of RGD motifs with respect to the total number of amino acids is more preferably at least 0.6%, still more preferably at least 0.8%, still further more preferably at least 1.0%, particularly preferably at least 1.2%, and most preferably at least 1.5%. The number of RGD motifs within a recombinant peptide is, per 250 amino acids, preferably at least 4, still more preferably at least 6, further more preferably at least 8, and particularly preferably 12 to 16. The proportion of RGD motifs being 0.4% corresponds to at least one RGD sequence per 250 amino acids. The number of RGD motifs is an integer, and therefore, gelatin formed of 251 amino acids needs to contain at least two RGD sequences in order to satisfy the characteristics of 0.4%. It is preferable that the recombinant gelatin of the present invention contains at least two RGD sequences per 250 amino acids, more preferably contains at least three RGD sequences per 250 amino acids, and still more preferably contains at least four RGD sequences per 250 amino acids. As a further aspect of the recombinant gelatin of the present invention, the recombinant gelatin contains preferably at least 4 RGD motifs, more preferably at least 6 RGD motifs, further more preferably at least 8 RGD motifs, and particularly preferably 12 to 16 RGD motifs.

In addition, the recombinant gelatin may be partially hydrolyzed.

The recombinant gelatin used in the present invention is preferably represented by Formula 1: A-[(Gly-X-Y)$_n$]$_m$-B. n pieces of X each independently represent any amino acid and n pieces of Y each independently represent any amino acid. m preferably represents an integer of 2 to 10 and more preferably represents an integer of 3 to 5. n is preferably an integer of 3 to 100, more preferably an integer of 15 to 70, and most preferably an integer of 50 to 65. A represents an arbitrary amino acid or an amino acid sequence, and B represents an arbitrary amino acid or an amino acid sequence. Here, n pieces of Gly-X-Y may be the same as or different from each other.

More preferably, the recombinant gelatin used in the present invention is represented by Gly-Ala-Pro-[(Gly-X-Y)$_{63}$]$_3$-Gly (SEQ ID NO: 11) (in the formula, 63 pieces of X each independently represent any amino acid and 63 pieces of Y each independently represent any amino acid. Here, 63 pieces of Gly-X-Y may be the same as or different from each other).

It is preferable that a plurality of sequence units of collagen which naturally exists are bonded to a repeating unit. Any naturally existing collagen referred to herein may be used as long as the collagen naturally exists, but is preferably I type collagen, II type collagen, III type collagen, IV type collagen, or V type collagen. More preferably, the collagen is I type collagen, II type collagen, or III type collagen. According to another form, the above-described collagen is preferably derived from a human, cattle, a pig, a mouse, or a rat, and is more preferably derived from a human.

An isoelectric point of the recombinant gelatin used in the present invention is preferably 5 to 10, more preferably 6 to 10, and further more preferably 7 to 9.5. The measurement of the isoelectric point of the recombinant gelatin is not particularly limited as long as it is a method capable of measuring a known isoelectric point, but can be carried out by measuring a pH after passing a 1 mass % of gelatin solution through a mixed crystal column of a cation-anion exchange resin by an isoelectric point electrophoresis method (refer to Maxey, C. R. (1976); Phitogr. Gelatin 2, Editor Cox, P. J. Academic, London, Engl.).

It is preferable that the recombinant gelatin is not deaminated.

It is preferable that the recombinant gelatin does not have a telopeptide.

It is preferable that the recombinant gelatin is a substantially pure polypeptide which is prepared using a nucleic acid encoding an amino acid sequence.

It is particularly preferable that the recombinant gelatin used in the present invention is any of;
(1) a peptide formed of an amino acid sequence described in SEQ ID NO: 1;
(2) a peptide which is formed of an amino acid sequence in which one or several amino acids are deleted, substituted, or added in the amino acid sequence disclosed in SEQ ID NO: 1, and has biocompatibility; or
(3) a peptide which is formed of an amino acid sequence having 80% or more (more preferably 85% or more, further more preferably 90% or more, particularly preferably 95% or more, and most preferably 98% or more) sequence identity to the amino acid sequence disclosed in SEQ ID NO: 1, and has biocompatibility.

The sequence identity in the present invention indicates a value calculated by the following formula.

% Sequence identity=[(number of identical residues)/(alignment length)]×100

The sequence identity between two amino acid sequences can be determined by any method known to those skilled in the art, and can be determined using the BLAST (Basic Local Alignment Search Tool) program (J. Mol. Biol. 215: 403-410, 1990) and the like.

"One or several" in the "amino acid sequence in which one or several amino acids are deleted, substituted, or added" preferably means 1 to 20 amino acids, more preferably means 1 to 10 amino acids, still more preferably means 1 to 5 amino acids, and particularly preferably means 1 to 3 amino acids.

The recombinant gelatin used in the present invention can be produced through gene recombination technology which is known to those skilled in the art, and can be produced in accordance with, for example, methods disclosed in EP1014176A2, U.S. Pat. No. 6,992,172B, WO2004/85473A, and WO2008/103041A. Specifically, a gene encoding an amino acid sequence of predetermined recombinant gelatin is acquired, the acquired gene is incorporated into an expression vector to produce a recombinant expression vector, and a transformant is produced by introducing the recombinant expression vector into an appropriate host. The recombinant gelatin is produced by culturing the obtained transformant in an appropriate medium. Therefore, it is possible to prepare the recombinant gelatin used in the present invention by collecting the recombinant gelatin produced from a culture product.

(1-4) Biocompatible Macromolecular Block

In the present invention, a block (aggregation) formed of the above-described biocompatible macromolecules is used.

The shape of the biocompatible macromolecular block in the present invention is not particularly limited. Examples thereof include an amorphous shape, a spherical shape, a particulate shape (granule), a powdery shape, a porous shape, a fibrous shape, a spindle shape, a flat shape, and a sheet shape. An amorphous shape, a spherical shape, a particulate shape (granule), a powdery shape, and a porous shape are preferable. The amorphous shape indicates that the shape of a surface is uneven, and indicates, for example, an object, such as rock, which has roughness. Examples of the above-described shapes are not distinct from each other. For example, in some cases, an example of a subordinate concept of the particulate shape (granule) is an amorphous shape.

The shape of the biocompatible macromolecular block in the present invention is not particularly limited as described above. However, the tap density is preferably 10 mg/cm$^3$ to 500 mg/cm$^3$, more preferably 20 mg/cm$^3$ to 400 mg/cm$^3$, still more preferably 40 mg/cm$^3$ to 220 mg/cm$^3$, and particularly preferably 50 mg/cm$^3$ to 150 mg/cm$^3$.

The tap density is a value indicating how much volume of block can be densely filled. It can be seen that, as the value becomes smaller, the block cannot be densely filled, that is, the structure of the block is complicated. It is considered that the tap density of the biocompatible macromolecular block indicates the complexity of a surface structure of the biocompatible macromolecular block and the amount of void formed in a case where biocompatible macromolecular blocks are collected as an aggregate. As the tap density becomes smaller, the void between biocompatible macromolecular blocks becomes larger and a grafted region of a cell becomes larger. In addition, in a case where the tap density is not too small, the biocompatible macromolecular block can appropriately exist between cells and nutrients can be delivered into a cell structure in a case where the cell structure is produced, and therefore, it is considered that it is appropriate that the tap density falls within the above-described range.

The tap density referred to in the present specification is not particularly limited, but can be measured as follows. A container (with a cylindrical shape with a diameter of 6 mm and a length of 21.8 mm: a capacity of 0.616 cm$^3$) (hereinafter, described as a cap) is prepared for the measurement of the tap density. First, the mass of only a cap is measured. Thereafter, a funnel is attached to the cap, and blocks are poured from the funnel so as to be collected in the cap. After placing a sufficient amount of block, the cap portion is hit 200 times on a hard object such as a desk, the funnel is removed, and the blocks are leveled with a spatula. The mass is measured in a state where the cap is filled up with the blocks. The tap density can be obtained by calculating the mass of only the blocks from the difference between the mass of the cap filled up with the blocks and the mass of only the cap, and dividing the mass of only the blocks by the volume of the cap.

The cross-linking degree of the biocompatible macromolecular block in the present invention is not particularly limited, but is preferably greater than or equal to 2, more preferably 2 to 30, still more preferably 4 to 25, and particularly preferably 4 to 22.

The method for measuring the cross-linking degree (the number of cross-linking per molecule) of the biocompatible macromolecular block is not particularly limited. However, in a case where the biocompatible macromolecule is CBE3, the cross-linking degree can be measured by the TNBS (2,4,6-trinitrobenzene sulfonic acid) method to be described in examples, for example. Specifically, a sample obtained by mixing biocompatible macromolecular blocks, a NaHCO$_3$ aqueous solution, and a TNBS aqueous solution, allowing the mixture to react for 3 hours at 37° C., and then, stopping the reaction, and a blank obtained by mixing biocompatible macromolecular blocks, a NaHCO$_3$ aqueous solution, and a TNBS aqueous solution and stopping a reaction immediately after the mixing were prepared. The cross-linking degree (the number of cross-linking times per molecule) can be calculated from the following (Formula 2) and (Formula 3) by measuring each absorbance (345 nm) of the sample and the blank which have been diluted with pure water.

$$(As-Ab)/14{,}600 \times V/w \qquad \text{(Formula 2)}$$

(Formula 2) represents the amount (molar equivalent) of lysine per 1 g of biocompatible macromolecular blocks.

(In the formula, as represents the sample absorbance, Ab represents the blank absorbance, V represents the reaction liquid amount (g), and w represents the mass (mg) of the biocompatible macromolecular blocks.)

$$1-(\text{sample (Formula 2)/uncross-linked macromolecule (Formula 2)}) \times 34 \qquad \text{(Formula 3)}$$

(Formula 3) represents the number of cross-linking times per molecule.

The water absorption rate of the biocompatible macromolecular block in the present invention is not particularly limited, but is preferably greater than or equal to 300%, more preferably greater than or equal to 400%, still more preferably greater than or equal to 500%, particularly preferably greater than or equal to 600%, and most preferably greater than or equal to 700%. An upper limit of the water absorption rate is not particularly limited, but is generally 4,000% or less, or 2,000% or less.

The method for measuring the water absorption rate of the biocompatible macromolecular block is not particularly limited. However, the water absorption rate of the biocompatible macromolecular block can be measured, for example, through the method in examples to be described below. Specifically, a 3 cm×3 cm nylon mesh bag is filled with about 15 mg of biocompatible macromolecular blocks at 25° C. and is swollen in ion exchange water for 2 hours. Then, the biocompatible macromolecular blocks are dried with air for 10 minutes, and the mass is measured at each stage to obtain the water absorption rate according to (Formula 4).

Water absorption rate=$(w2-w1-w0)/w0$ (Formula 4)

(In the formula, w0 represents the mass of a material before water absorption, w1 represents the mass of an empty bag after water absorption, and w2 represents the mass of the entirety of the bag containing the material after water absorption.)

The size of one biocompatible macromolecular block in the present invention is not particularly limited, but is preferably 10 μm to 300 μm, more preferably 20 μm to 200 μm, more preferably 20 μm to 150 μm, still more preferably 50 μm to 120 μm, and particularly preferably 53 μm to 106 μm.

It is possible to favorably deliver nutrients into a cell structure from the outside by setting the size of one biocompatible macromolecular block to be within the above-described range. The size of one biocompatible macromolecular block does not mean that an average value of the sizes of a plurality of biocompatible macromolecular blocks is within the above-described range, but means the size of each biocompatible macromolecular block which is obtained by sieving a plurality of biocompatible macromolecular blocks.

The size of one block can be defined by the size of a sieve used in a case of dividing the block. For example, blocks remaining on a sieve with 106 μm in a case where blocks which have been passed through a sieve with 180 μm for sifting are sifted using the sieve with 106 μm can be regarded as blocks having a size of 106 to 180 μm. Next, blocks remaining on a sieve with 53 μm in a case where blocks which have been passed through the sieve with 106 μm for sifting are sifted using the sieve with 53 μm can be regarded as blocks having a size of 53 to 106 μm. Next, blocks remaining on a sieve with 25 μm in a case where blocks which have been passed through the sieve with 53 μm for sifting are sifted using the sieve with 25 μm can be regarded as blocks having a size of 25 to 53 μm.

(1-5) Method for Producing Biocompatible Macromolecular Block

The method for producing a biocompatible macromolecular block is not particularly limited. For example, it is possible to obtain a biocompatible macromolecular block by pulverizing a solid matter (such as a porous body of biocompatible macromolecules) containing a biocompatible macromolecule using a pulverizer (such as NEW POWER-MILL). The solid matter (such as a porous body of a biocompatible macromolecule) containing a biocompatible macromolecule can be obtained, for example, by freeze-drying an aqueous solution containing the biocompatible macromolecule.

It is possible to produce an amorphous biocompatible macromolecular block of which the shape of the surface is uneven, by pulverizing a solid matter containing a biocompatible macromolecule as described above.

The method for producing a porous body of a biocompatible macromolecule is not particularly limited, but it can also be obtained by freeze-drying an aqueous solution containing the biocompatible macromolecule. For example, by including a freezing step in which the liquid temperature of the portion with the highest liquid temperature in the solution (internal maximum liquid temperature) becomes "a solvent melting point −3° C." or less in an unfrozen state, formed ice has a spherical shape. Through this step, the ice is dried to obtain a porous body having spherical isotropic pores (spherical pores). By performing freezing without including a freezing step in which the liquid temperature of the portion with the highest liquid temperature in the solution (internal maximum liquid temperature) becomes "a solvent melting point −3° C." or more in an unfrozen state, the formed ice can have a pillar/flat plate shape. Through this step, in a case where the ice is dried, a porous body having long columnar or flat plate pores (column/flat plate pores) on one axis or two axes is obtained. In a case where a biocompatible macromolecular block is produced by pulverizing a porous body of a biocompatible macromolecule, pores of the porous body before the pulverization have an influence on the shape of the obtained biocompatible macromolecular block. Therefore, as described above, it is possible to adjust the shape of the obtained biocompatible macromolecular block by adjusting freeze-drying conditions.

As an example of the method for producing a porous body of a biocompatible macromolecule, a method including:

(A) a step of cooling a solution of biocompatible macromolecules under the conditions where the difference between the temperature of a portion having the highest liquid temperature within the solution and the temperature of a portion having the lowest liquid temperature within the solution is lower than or equal to 2.5° C., and the temperature of a portion having the highest liquid temperature within the solvent is lower than or equal to a melting point, to an unfrozen state;

(B) a step of freezing the solution of the biocompatible macromolecules obtained in the step (A); and (C) a step of freeze-drying the frozen biocompatible macromolecules obtained in the step (B).

However, the method is not limited to the above method.

In a case where the solution of the biocompatible macromolecules is cooled to an unfrozen state, the variation in the size of obtained pore of porous body is reduced by making the difference between the temperature of a portion having the highest liquid temperature and the temperature of a portion having the lowest liquid temperature within the solution be lower than or equal to 2.5° C. (preferably lower than or equal to 2.3° C. and more preferably lower than or equal to 2.1° C.), that is, by reducing the difference in temperature. A lower limit of the difference between the temperature of a portion with the highest liquid temperature and the temperature of a portion with the lowest liquid temperature in the solution is not particularly limited as long as the difference is 0° C. or more, but may be 0.1° C. or more, 0.5° C. or more, 0.8° C. or more, or 0.9° C. or more. In this manner, the cell structure obtained by using the biocompatible macromolecular block produced by using the produced porous body achieves an effect of exhibiting a high cell number.

The cooling in the step (A) is preferably carried out, for example, using a material (preferably, TEFLON (registered trademark)) having a lower thermal conductivity than water. The portion having the highest liquid temperature within the solution can be supposed as the farthest portion from a cooling side, and the portion having the lowest liquid temperature within the solution can be supposed as a liquid temperature of the cooling surface.

In the step (A), the difference between the temperature of a portion having the highest liquid temperature within the solution and the temperature of a portion having the lowest liquid temperature within the solution immediately before generation of solidification heat is preferably lower than or equal to 2.5° C., more preferably lower than or equal to 2.3° C., and still more preferably lower than or equal to 2.1° C. Here, the "difference in temperature immediately before the generation of solidification heat" means a difference in temperature in a case where the difference in temperature becomes largest between 1 second and 10 seconds before the generation of solidification heat.

In the step (A), the temperature of a portion having the lowest liquid temperature within the solution is preferably lower than or equal to a melting point of a solvent −5° C., more preferably lower than or equal to a melting point of a solvent −5° C. and higher than or equal to a melting point of a solvent −20° C., and still more preferably lower than or equal to a melting point of a solvent −6° C. and higher than or equal to a melting point of a solvent −16° C. The solvent of a melting point of a solvent is a solvent of a solution of biocompatible macromolecules.

In the step (B), the solution of the biocompatible macromolecules obtained in the step (A) is frozen. The cooling temperature for the freezing in the step (B) is not particularly limited. Depending on cooling equipment, the cooling temperature is preferably a temperature which is 3° C. to 30° C. lower than the temperature of a portion having the lowest liquid temperature within the solution, more preferably a temperature which is 5° C. to 25° C. lower than the temperature of a portion having the lowest liquid temperature within the solution, and still more preferably a temperature which is 10° C. to 20° C. lower than the temperature of a portion having the lowest liquid temperature within the solution.

In Step (C), the frozen biocompatible macromolecules obtained in Step (B) are freeze-dried. The freeze-drying can be performed through a usual method. For example, the freeze-drying can be performed by carrying out vacuum drying at a temperature lower than a melting point of a solvent and further carrying out vacuum drying at room temperature (20° C.).

In the present invention, a biocompatible macromolecular block can be preferably produced by pulverizing the porous body obtained in the above-described Step (C). That is, the biocompatible macromolecular block may be preferably in the form of granules obtained by pulverizing a porous body of the biocompatible macromolecules.

(2) Cell

The cells used in the present invention are mesenchymal stem cells. In addition, one kind of mesenchymal stem cell may be used, or a plurality of kinds of cells may be used in combination.

The mesenchymal stem cells (MSCs) used in the present invention are cells that have the ability to replicate as undifferentiated cells and have the ability to differentiate into bone cells, chondrocytes, cardiomyocytes, adipocytes, and the like. The origin of the mesenchymal stem cells is not particularly limited, and may be human mesenchymal stem cells or mesenchymal stem cells derived from non-human animals such as mice, rats, cats, or dogs.

It is known that mesenchymal stem cells can be obtained from various tissues such as bone marrow, cartilage, adipose tissue, placental tissue, umbilical cord tissue, and dental pulp, and their origin is not particularly limited. As the mesenchymal stem cells, fat-derived mesenchymal stem cells and bone marrow-derived mesenchymal stem cells are preferable, and fat-derived mesenchymal stem cells are more preferable. The mesenchymal stem cells are preferably derived from humans or dogs. The mesenchymal stem cells may be autologous cells of a patient to be administered or allogeneic cells.

As a method for isolating mesenchymal stem cells from each tissue, a known method in the related art can be adopted. For example, mesenchymal stem cells can be appropriately separated from tissues by a collagenase method. For example, mesenchymal stem cells can be collected using cell surface markers (CD105, CD73, CD90, and the like) as indicators.

(3) Cell Structure

The cell structure according to the present invention is a cell structure that includes a plurality of the above-mentioned biocompatible macromolecular blocks and at least one kind of a plurality of mesenchymal stem cells, in which the above macromolecular blocks arranged in a gap between the plurality of the mesenchymal stem cells. In the present invention, by three-dimensionally arranging a plurality of macromolecular blocks in a gap between a plurality of cells in a mosaic shape using biocompatible macromolecular blocks and mesenchymal stem cells, the plurality of biocompatible macromolecular blocks and the cells are three-dimensionally arranged in a mosaic manner, and thereby a three-dimensional cell structure in which cells are uniformly present in the structure is formed and the structure has a substance-permeating ability.

In the cell structure of the present invention, the plurality of macromolecular blocks are arranged in a gap between the plurality of cells. Here, the "gap between cells" is not necessarily a space closed by the constituent cells, and may be interposed by the cells. Gaps are not necessarily present between all of the cells, and there may be a place where cells are brought into contact with each other. The distance of the gap between cells through macromolecular blocks, that is, the gap distance in a case of selecting a certain cell, and a cell existing in the shortest distance from the certain cell is not particularly limited. However, the distance is preferably the size of a macromolecular block, and an appropriate distance is also within the range of the appropriate size of a macromolecular block.

In addition, the macromolecular blocks in the present invention have a configuration of being interposed by the cells. However, there are not necessarily cells between all of the macromolecular blocks, and there may be a place where macromolecular blocks are brought into contact with each other. The distance between the macromolecular blocks through cells, that is, the distance in a case of selecting a macromolecular block, and a macromolecular block existing in the shortest distance from the macromolecular block is not particularly limited. However, the distance is preferably the size of an aggregation of cells in a case where one or several cells to be used are gathered. For example, the size thereof is 10 μm to 1,000 μm, preferably 10 μm to 100 μm, and more preferably 10 μm to 50 μm.

In the present specification, the expression "uniformly present" such as "three-dimensional cell structure in which cells are uniformly present in the structure" is used, but this does not mean complete uniformity.

The thickness or diameter of the cell structure in the present invention can be a desired size, but the lower limit is preferably 100 μm or more, more preferably 150 μm or more, and still more preferably 215 μm or more, still more preferably 400 μm or more, and most preferably 730 μm or more. The upper limit of the thickness or diameter is not particularly limited, but a general range in use is preferably 3 cm or less, more preferably 2 cm or less, and still more preferably 1 cm or less. In addition, the thickness or diameter of the cell structure is preferably 150 μm to 3 cm, more preferably 400 μm to 3 cm, still more preferably 500 μm to 2 cm, and further more preferably 720 μm to 1 cm.

In the cell structure in the present invention, preferably, a region formed of macromolecular blocks and a region formed of cells are arranged in a mosaic shape. In the present specification, the "thickness or diameter of the cell structure" indicates the following. In a case where a certain point A in the cell structure is selected, the length of a line that divides the cell structure within a straight line passing through the point A so that the distance from the outside of the cell structure is minimized is set to line A. A point A where the line A is the longest in the cell structure is selected, and the length of the line A at that time is defined as "the thickness or diameter of the cell structure".

In the cell structure in the present invention, the ratio of a macromolecular block to a cell is not particularly limited. However, the mass of a macromolecular block per cell is preferably 0.0000001 μg to 1 μg, more preferably 0.000001 μg to 0.1 μg, still more preferably 0.00001 μg to 0.01 μg, and most preferably 0.00002 μg to 0.006 μg. By making the ratio be within the above-described range, cells can be more uniformly present. In addition, by setting the lower limit to be within the above-described range, it is possible to exhibit an effect of the cells in a case of using the cells for the above-described use. Moreover, by setting the upper limit to be within the above-described range, it is possible to supply components in arbitrarily existing macromolecular blocks to cells. Here, the components in macromolecular blocks are not particularly limited, but examples thereof include components contained in a medium to be described later.

(4) Method for Producing Cell Structure

The cell structure can be produced by mixing a biocompatible macromolecular block and at least one kind of cell. More specifically, the cell structure can be produced by alternately arranging a biocompatible macromolecular block (an aggregation formed of biocompatible macromolecules) and a cell. The term "alternately" does not mean complete alternation, but means, for example, a state in which biocompatible macromolecular block and cells are mixed. The production method is not particularly limited, but is preferably a method of forming a macromolecular block and then seeding cells. Specifically, a cell structure can be produced by incubating a mixture of a biocompatible macromolecular block and a cell-containing culture solution. For example, in a container, cells and biocompatible macromolecular blocks prepared in advance are arranged in a mosaic shape in a liquid held in the container. As means for arrangement, it is preferable to promote and control the formation of a mosaic array formed of cells and biocompatible macromolecular blocks by using natural aggregation, natural fall, centrifugation, and stirring.

The container used is preferably a container made of a low cell adhesive material or a cell non-adhesive material, and more preferably a container made of polystyrene, polypropylene, polyethylene, glass, polycarbonate, or polyethylene terephthalate. The shape of the bottom surface of the container is preferably a flat bottom shape, a U shape, or a V shape.

As for the mosaic-like cell structure obtained by the above method, it is possible to produce a cell structure having a desired size by a method of (i) fusing separately prepared mosaic-like cell aggregation, or (ii) increasing the volume in a differentiation medium or a growth medium. The method of fusing and the method of increasing the volume are not particularly limited.

For example, in the step of incubating a mixture of the biocompatible macromolecular block and the cell-containing culture solution, the volume of the cell structure can be increased by replacing the medium with a differentiation medium or a growth medium. Preferably, in the step of incubating the mixture of the biocompatible macromolecular block and the cell-containing culture solution, it is possible to produce a cell structure in which cells are uniformly present in the cell structure having a desired size by further adding the biocompatible macromolecular block.

The method of fusing the separately prepared mosaic-like cell aggregation is specifically a method for producing a cell structure, including a step of fusing a plurality of cell structures which include a plurality of biocompatible macromolecular blocks and a plurality of mesenchymal stem cells and in which one or plurality of the biocompatible macromolecular blocks are arranged in a portion or the entirety of a plurality of gaps formed by the plurality of mesenchymal stem cells.

[Regarding Step (b)]

The step (b) is a step of culturing any one or more of the mesenchymal stem cells before the incubation in the step (a), the mesenchymal stem cells incubated in the step (a), and the cell structure produced in the step (a) in a medium containing a GLP-1 receptor agonist.

As described above, the step (b) may be performed before the step (a), the step (b) and the step (a) may be performed at the same time, and the step (b) may be performed after the step (a). In addition, the step (b) can be performed by at least any one of before the step (a), at the same time as the step (a), after the step (a). That is, the step (b) may be performed before the step (a) and at the same time as the step (a), may be performed before the step (a) and after the step (a), may be performed at the same time as the step (a) and after the step (a), or may be performed before the step (a), at the same time as the step (a), and after the step (b). In a case where the step (b) is performed before the step (a), the mesenchymal stem cells before the incubation in the step (a) are cultured in a medium containing a GLP-1 receptor agonist, and then the step (a) is performed using mesenchymal stem cells cultured in a medium containing a GLP-1 receptor agonist to produce a cell structure. In a case where the step (b) and the step (a) are performed at the same time, a plurality of pieces of biocompatible macromolecular blocks and a plurality of pieces of mesenchymal stem cells are incubated in a medium containing a GLP-1 receptor agonist to produce a cell structure which includes a plurality of biocompatible macromolecular blocks and a plurality of pieces of mesenchymal stem cells and in which at least one of the biocompatible macromolecular blocks is arranged in a gap between the plurality of mesenchymal stem cells. In a case where the step (b) is performed after the step (a), a cell structure is first produced in the step (a), and then the cell structure produced in the step (a) is cultured in a medium containing a GLP-1 receptor agonist.

The medium in the step (b) is a medium containing a GLP-1 receptor agonist. The kind of the medium is not particularly limited as long as the medium can maintain or expand mesenchymal stem cells. Examples thereof include MesenPro (containing 2% serum, Life Technologies), Dulbecco's modified Eagle medium (DMEM)/F12 (containing 20% fetal bovine serum (FBS) (Gibco), Life Technologies), DMEM (containing 10% FBS (Gibco), SIGMA), PRIME-XV XSFM (serum-free, JX Energy), MSCGM BulletKit (registered trademark) (Takara Bio), Mesencult-ACF (containing no animal-derived components), Mesencult-SF (serum-free, all of Veritas), MSCGM BulletKit (containing serum, Lonza), and the like.

Examples of the GLP-1 receptor agonist include GLP-1, GLP-1 analogs, and other substances that promote signal transduction through the GLP-1 receptor (such as peptides or low molecular compounds). Examples of the GLP-1 analog include exenatide (exendin-4), exenatide LAR (long acting release: long acting release formulation of exenatide), liraglutide, taspoglutide, semaglutide, albiglutide, lixisenatide, dulaglutide, and the like.

As the exendin-4, the GLP-1 receptor agonist is preferable.

The content of the GLP-1 receptor agonist (preferably Exendin-4) in the medium in Step (b) is preferably 1 nmol/L to 100 nmol/L, more preferably 2 nmol/L to 50 nmol/L, and still more preferably 5 nmol/L to 20 nmol/L.

The medium in Step (b) can contain at least one selected from activin A, albumin, B27-supplement (Gibco), or N2-supplement (Gibco), in addition to the GLP-1 receptor agonist, and preferably contains activin A. The medium used in Step (b) particularly preferably contains all of activin A, albumin, B27-supplement (Gibco), or N2-supplement (Gibco).

In a case where the medium in Step (b) contains activin A, the content of activin A in the medium is preferably 5 ng/mL to 500 ng/mL, more preferably 10 ng/mL to 200 ng/mL, and still more preferably 20 ng/mL to 100 ng/mL.

In a case where the medium in Step (b) contains albumin, the content of albumin in the medium is preferably 0.1 mass % to 10 mass %, more preferably 0.2 mass % to 5 mass %, and still more preferably 0.5 mass % to 2 mass %.

In a case where the medium in Step (b) contains B27-supplement (Gibco), the content of B27-supplement in the medium is preferably 0.1 mass % to 10 mass %, more preferably 0.2 mass % to 5 mass %, and still more preferably 0.5 mass % to 2 mass %.

In a case where the medium in Step (b) contains N2-supplement (Gibco), the content of N2-supplement in the medium is preferably 0.1 mass % to 10 mass %, more preferably 0.2 mass % to 5 mass %, and still more preferably 0.5 mass % to 2 mass %.

In Step (b), the cells or cell structures are preferably cultured for 3 to 14 days, and more preferably cultured for 7 to 9 days.

As the culture condition in Step (b), general cell culture conditions may be selected. Conditions of 37° C. and 5% $CO_2$ are exemplified. During the culture, the medium is preferably changed at an appropriate interval (preferably once every 1 to 7 days, more preferably once every 3 to 4 days).

For the culture, a cell culture container such as a plate, a dish, a cell culture flask, and a cell culture bag can be used. It is appropriate that the cell culture bag has gas permeability. In a case where a large amount of cells is required, a large culture tank may be used. The culture can be performed in either of an open system or a closed system.

[Regarding Step (c)]

The step (c) is a step of culturing the cell structure obtained in the step (a) or the step (b) in a medium containing a water-soluble vitamin and hepatocyte growth factor (HGF).

The medium in the step (c) is a medium containing a water-soluble vitamin and hepatocyte growth factor (HGF). The kind of the medium is not particularly limited as long as the medium can maintain or expand mesenchymal stem cells. Examples thereof include MesenPro (containing 2% serum, Life Technologies), Dulbecco's modified Eagle medium (DMEM)/F12 (containing 20% fetal bovine serum (FBS) (Gibco), Life Technologies), DMEM (containing 10% FBS (Gibco), SIGMA), PRIME-XV XSFM (serum-free, JX Energy), MSCGM BulletKit (registered trademark) (Takara Bio), Mesencult-ACF (containing no animal-derived components), Mesencult-SF (serum-free, all of Veritas), MSCGM BulletKit (containing serum, Lonza), and the like.

Examples of the water-soluble vitamin include vitamin C; vitamin B1; vitamin B2; vitamin B3 containing niacin or nicotinamide; vitamin B5; vitamin B6; vitamin B7; vitamin B9; and vitamin B12. As the water-soluble vitamin, nicotinamide is preferable.

The content of the water-soluble vitamin (preferably nicotinamide) in the medium in Step (c) is preferably 1 mmol/L to 100 mmol/L, more preferably 2 mmol/L to 50 mmol/L, and still more preferably 5 mmol/L to 20 mmol/L.

The content of the hepatocyte growth factor (HGF) in the medium in Step (c) is preferably 5 ng/mL to 500 ng/mL, more preferably 10 ng/mL to 200 ng/mL, and still more preferably 20 ng/mL to 100 ng/mL.

The medium in Step (c) can contain a histone deacetylation (HDAC) inhibitor in addition to the water-soluble vitamin and the hepatocyte growth factor (HGF). The medium in Step (c) preferably contains a histone deacetylation (HDAC) inhibitor.

Examples of the histone deacetylation (HDAC) inhibitor include (1) fatty acids such as butyric acid, O-hydroxybutyric acid, valproic acid, salts and esters thereof, (2) hydroxamic acids such as trichostatin A, oxamflatin, and suberoylanilide, (3) cyclic peptides such as trapoxin, apicidin, and FK228, and (4) benzamide, and the like. As the histone deacetylation (HDAC) inhibitor, valproic acid is preferable.

In a case where the medium in Step (c) contains valproic acid, the content of valproic acid in the medium is preferably 0.1 mmol/L to 10 mmol/L, more preferably 0.2 mmol/L to 5 mmol/L, and more preferably 0.5 mmol/L to 2 mmol/L.

The medium in Step (c) may include one or more selected from GLP-1 receptor agonist, activin A, albumin, B27-supplement (Gibco), or N2-supplement (Gibco), similarly to the medium in Step (b). The medium in Step (c) particularly preferably contains all of the GLP-1 receptor agonist, activin A, albumin, B27-supplement (Gibco), and N2-supplement (Gibco).

In a case where the medium in Step (c) contains a GLP-1 receptor agonist, the content of the GLP-1 receptor agonist in the medium is preferably 1 nmol/L to 100 nmol/L, more preferably 2 nmol/L to 50 nmol/L, and still more preferably 5 nmol/L to 20 nmol/L.

In a case where the medium in Step (c) contains activin A, the content of activin A in the medium is preferably 5 ng/mL to 500 ng/mL, more preferably 10 ng/mL to 200 ng/mL, and still more preferably 20 ng/mL to 100 ng/mL.

In a case where the medium in Step (c) contains albumin, the content of albumin in the medium is preferably 0.1 mass % to 10 mass %, more preferably 0.2 mass % to 5 mass %, and still more preferably 0.5 mass % to 2 mass %.

In a case where the medium in Step (c) contains B27-supplement (Gibco), the content of B27-supplement in the medium is preferably 0.1 mass % to 10 mass %, more preferably 0.2 mass % to 5 mass %, and still more preferably 0.5 mass % to 2 mass %.

In a case where the medium in Step (c) contains N2-supplement (Gibco), the content of N2-supplement in the medium is preferably 0.1 mass % to 10 mass %, more preferably 0.2 mass % to 5 mass %, and still more preferably 0.5 mass % to 2 mass %.

In Step (c), the cell structure is preferably cultured for 7 to 35 days, and more preferably cultured for 14 to 28 days.

As the culture conditions in Step (c), general cell culture conditions may be selected. Conditions of 37° C. and 5% $CO_2$ are exemplified. During the culture, the medium is preferably changed at an appropriate interval (preferably once every 1 to 7 days, more preferably once every 3 to 4 days).

For the culture, a cell culture container such as a plate, a dish, a cell culture flask, and a cell culture bag can be used. It is appropriate that the cell culture bag has gas permeability. In a case where a large amount of cells is required, a large culture tank may be used. The culture can be performed in either of an open system or a closed system.

According to the present invention, insulin-producing cells can be produced from mesenchymal stem cells by the step (a), the step (b), and the step (c) described above. The insulin-producing cell means a cell that has an ability to synthesize insulin and secrete it out of the cell.

[Insulin-Producing Cell, Cell Structure Containing Insulin-Producing Cell, and Pharmaceutical Composition]

According to the present invention, there is provided an insulin-producing cell produced by the method for producing an insulin-producing cell from mesenchymal stem cells, including the step (a), the step (b), and the step (c), and a cell structure including the insulin-producing cell. According to the present invention, there is provided a pharmaceutical composition including the insulin-producing cell or the cell structure.

In the insulin-producing cells and the cell structure, Stimulation Index, obtained by dividing a concentration of insulin in a medium when the cell structure containing $5\times10^5$ insulin-producing cells was cultured in a 2 mL of Krebs-Ringer bicarbonate buffer at a concentration of 20 mmol/L glucose for 60 minutes with a concentration of insulin in a medium when the cell structure was cultured in a 2 mL of Krebs-Ringer bicarbonate buffer at a concentration of 3 mmol/L glucose for 60 minutes, is preferably 2.0 or more, more preferably 2.5 or more, still more preferably 3.0 or more, and particularly preferably 3.4 or more.

The pharmaceutical composition of the present invention may contain a pharmaceutically acceptable carrier or additive in addition to the insulin-producing cell or the cell structure. Examples of the pharmaceutically acceptable carrier or additive include a diluent or buffer (for example, water, usually physiological salt solution), a chelating agent (for example, ethylenediamine tetraacetic acid (EDTA)), a buffer (for example, acetate, citrate, or phosphate); active substances for adjusting tonicity (for example, sodium chloride or dextrose), but are not particularly limited.

In the present invention, the insulin-producing cell, the cell structure containing the insulin-producing cell, or the pharmaceutical composition can be transplanted into a subject requiring insulin therapy.

Disease states that require insulin therapy include:
type 1 diabetes, insulin-dependent type 2 diabetes,
diabetic coma,
complications of severe infection, moderate or more severe surgery, and pregnancy with diabetes,
and the like, but are not particularly limited.

The pharmaceutical composition of the present invention can be preferably used as a therapeutic agent for diabetes.

As the transplantation method, it is possible to use incision, injection, and endoscope. Unlike a cell transplant such as a cell sheet, the cell structure containing insulin-producing cells can reduce the size of the structure, and thus a minimally invasive transplantation method such as transplantation by injection is possible.

The amount of insulin-producing cells or a cell structure containing the insulin-producing cells when being transplanted can be appropriately selected depending on the state of the transplant target (human or animal) and the like. The number of the cells to be transplanted is preferably $1.0\times10^5$ cells/kg to $2.0\times10^{10}$ cells/kg, and more preferably $1.0\times10^6$ cells/kg to $2.0\times10^9$ cells/kg. Regarding the number of transplantation of the insulin-producing cells or the cell structure containing the insulin-producing cells, the transplantation may be performed only once, or may be performed two or more times depending on the necessity.

According to the present invention, the following inventions are provided.

(A) A method for treating a disease state (preferably diabetes) requiring insulin therapy, including administering the insulin-producing cell of the present invention or the cell structure of the present invention to a subject requiring insulin therapy.

(B) The insulin-producing cell of the present invention or the cell structure of the present invention for use in treating a disease state (preferably diabetes) requiring insulin therapy.

(C) Use of the insulin-producing cell of the present invention or the cell structure of the present invention for producing a pharmaceutical composition (preferably, therapeutic agent for diabetes).

The present invention will be more specifically described using the following examples, but is not limited by the examples.

EXAMPLES

[Reference Example 1] Recombinant Peptide (Recombinant Gelatin)

The following CBE3 (disclosed in WO2008/103041A) as recombinant peptides (recombinant gelatin).

CBE3:

Molecular weight: 51.6 kD

Structure: GAP [(GXY)$_{63}$]$_3$G (SEQ ID NO: 11)

Amino acid number: 571

RGD sequence: 12

Imino acid content: 33%

Almost 100% of amino acids have a GXY repeating structure. In the amino acid sequence of CBE3, serine, threonine, asparagine, tyrosine, and cysteine are not included. CBE3 has an ERGD (SEQ ID NO: 10) sequence.

Isoelectric point: 9.34

GRAVY value: −0.682

1/IOB value: 0.323

Amino acid sequence (SEQ ID No: 1 in a sequence table) (which is the same as that of SEQ ID No: 3 in WO2008/103041A. However, X in the end is corrected to "P")

```
GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)₃G
```

[Reference Example 2] Production of Porous Body of Recombinant Peptide

[PTFE Thickness•Cylindrical Container]

A cylindrical cup-shaped polytetrafluoroethylene (PTFE) container having a bottom surface thickness of 3 mm, a diameter of 51 mm, a side surface thickness of 8 mm, and a height of 25 mm was prepared. In a case where the curved surface of the cylindrical cup is set as a side surface, the side surface is closed by PTFE of 8 mm and the bottom surface (circular shape of a flat plate) is also closed by PTFE of 3 mm. On the contrary, the upper surface is in an open shape. Accordingly, the inner diameter of the cylindrical cup is set to 43 mm. Hereinafter, this container is referred to as a PTFE thickness•cylindrical container.

[Aluminum Glass Plate•Cylindrical Container]

A cylindrical cup-shaped aluminum container having a thickness of 1 mm and a diameter of 47 mm was prepared. In a case where the curved surface of the cylindrical cup is set as a side surface, the side surface is closed by aluminum of 1 mm and the bottom surface (circular shape of a flat plate) is also closed by aluminum of 1 mm. On the contrary, the upper surface is in an open shape. In addition, TEFLON (registered trademark) with a thickness of 1 mm is evenly spread only in the inside of the side surface, and as a result, the inner diameter of the cylindrical cup becomes 45 mm. In addition, this container comes into a state where a 2.2 mm-glass plate is joined to the bottom surface thereof in addition to aluminum. Hereinafter, this container is referred to as an aluminum glass cylindrical container.

[Freezing Step in which Difference in Temperature is Small, and Drying Step]

An aqueous CBE3 solution was made to flow into a PTFE thickness•cylindrical container or an aluminum glass plate and cylindrical container, and the aqueous CBE3 solution was cooled from the bottom surface in a vacuum freeze dryer (TF5-85ATNNN: Takara Co., Ltd.) using a cooling shelf. A combination of the setting of the container, the final concentration of the aqueous CBE3 solution, the amount of solution, and the temperature of the shelf was prepared as described below.

Condition A:

PTFE thickness•cylindrical container, final concentration of aqueous CBE3 solution of 4 mass %, amount of aqueous solution of 4 mL. As the setting of the temperature of the shelf, the temperature was cooled until the temperature reached −10° C., and then freezing was performed for 1 hour at −10° C., for 2 hours at −20° C., for 3 hours at −40° C., and finally for 1 hour at −50° C. Thereafter, the present frozen product was subjected to vacuum drying for 24 hours at −20° C. after the setting of the temperature of the shelf returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased ($1.9 \times 10^5$ Pa). Then, the product was taken out of the vacuum freeze dryer. Accordingly, a porous body was obtained.

Condition B:

Aluminum/glass plate/cylindrical container, final concentration of aqueous CBE3 solution of 4 mass %, amount of aqueous solution of 4 mL. As the setting of the temperature of the shelf, the temperature was cooled until the temperature reached −10° C., and then freezing was performed for 1 hour at −10° C., for 2 hours at −20° C., for 3 hours at −40° C., and finally for 1 hour at −50° C. Thereafter, the present frozen product was subjected to vacuum drying for 24 hours at −20° C. after the setting of the temperature of the shelf returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased ($1.9 \times 10^5$ Pa). Then, the product was taken out of the vacuum freeze dryer. Accordingly, a porous body was obtained.

Condition C:

PTFE thickness•cylindrical container, final concentration of aqueous CBE3 solution of 4 mass %, amount of aqueous solution of 10 mL. As the setting of the temperature of the shelf, the temperature was cooled until the temperature reached −10° C., and then freezing was performed for 1 hour at −10° C., for 2 hours at −20° C., for 3 hours at −40° C., and finally for 1 hour at −50° C. Thereafter, the present frozen product was subjected to vacuum drying for 24 hours at −20° C. after the setting of the temperature of the shelf returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased ($1.9 \times 10^5$ Pa). Then, the product was taken out of the vacuum freeze dryer. Accordingly, a porous body was obtained.

[Measurement of Temperature in Each Freezing Step]

Regarding the conditions A to C, the liquid temperature of the surface of water in a center portion of a circle within a container was measured as the liquid temperature (non-cooled surface liquid temperature) of the farthest portion from a cooling side in a solution, and the liquid temperature of a bottom portion within the container was measured as the liquid temperature (cooled surface liquid temperature) of the closest portion to the cooling side in the solution.

Figure 2:
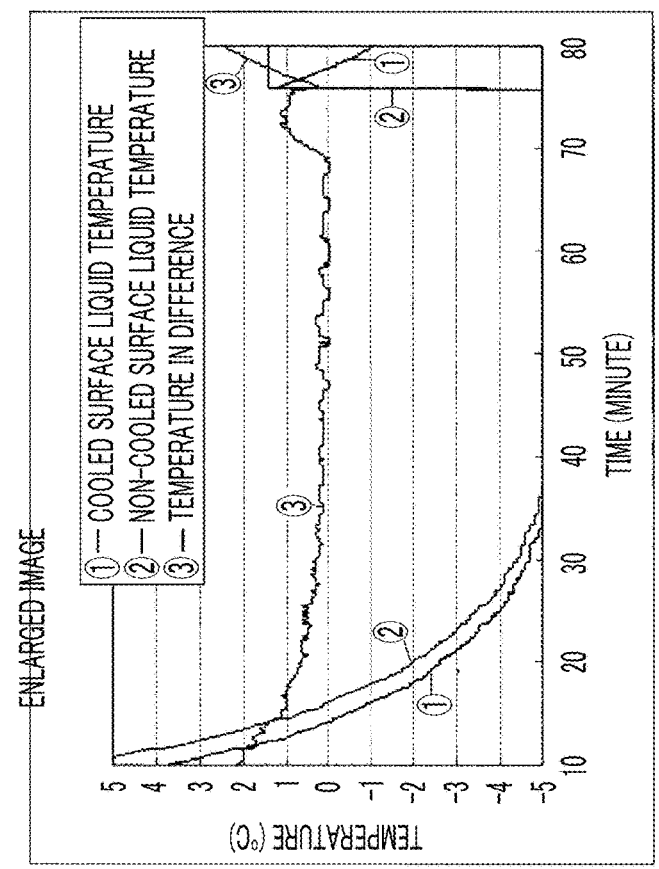
FIG. 2 shows a liquid temperature profiling of an experiment described in Condition B.
Figure 2:
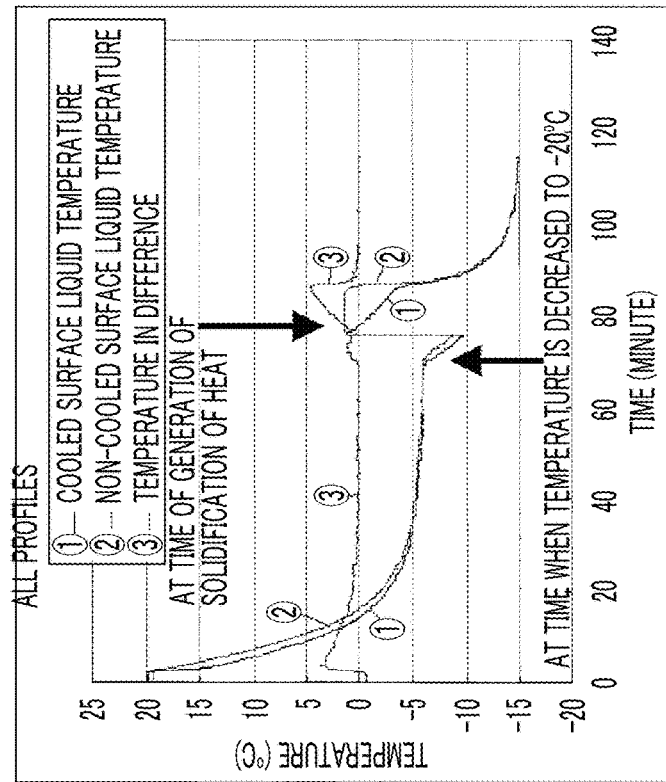
Figure 3:
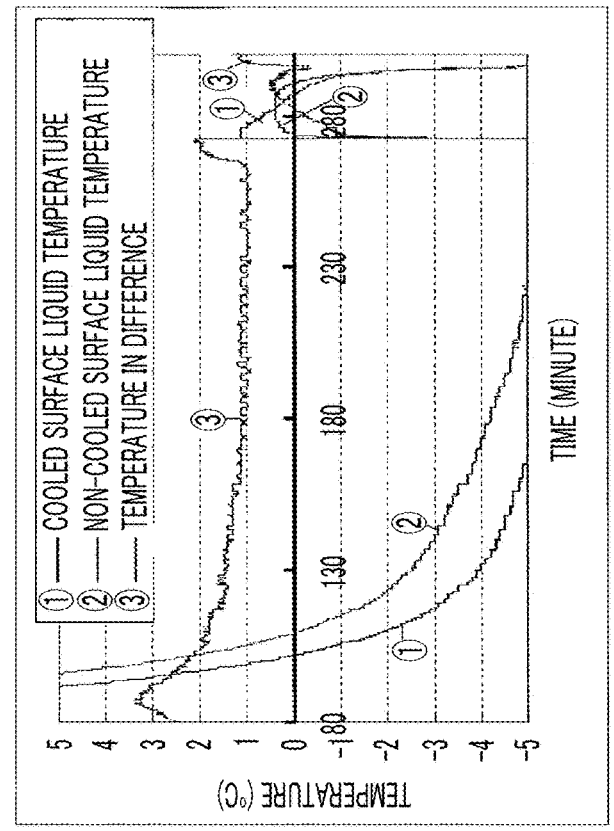
FIG. 3 shows a liquid temperature profiling of an experiment described in Condition C.
Figure 3:
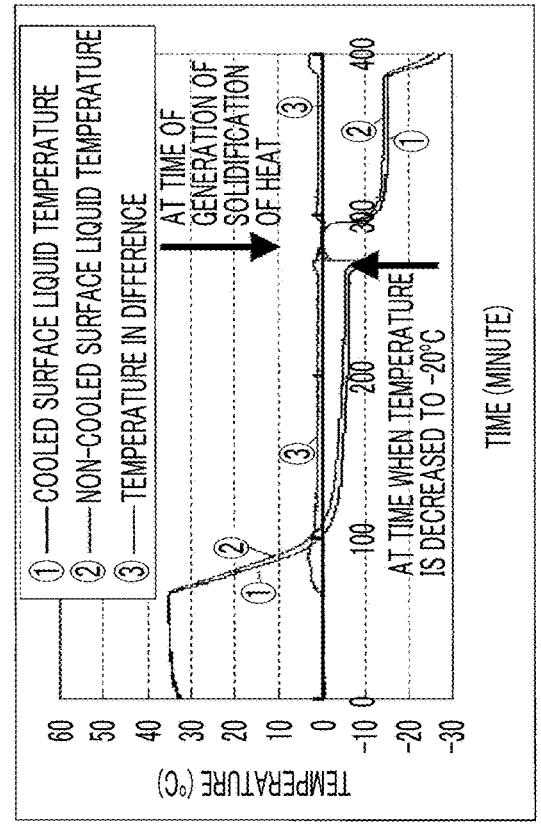

As a result, each temperature and a profile of the difference in temperature are as shown in FIGS. 1 to 3.

It can be seen from FIGS. 1 to 3 that the liquid temperature falls below 0° C., which is a melting point, in a setting section of the temperature of a shelf of −10° C. (before the temperature decreases to −20° C.) in the conditions A to C, and the solution enters a (unfrozen and overcooled) state where freezing does not occur in that state. In addition, in this state, the difference in temperature between the cooled surface liquid temperature and the non-cooled surface liquid temperature is less than or equal to 2.5° C. In the present specification, the "difference in temperature" means "non-cooled surface liquid temperature"-"cooled surface liquid temperature". Thereafter, the timing at which the liquid temperature rapidly rises to around 0° C. by further lowering the temperature of the shelf to −20° C. is confirmed. Here, it can be seen that freezing starts due to generation of solidification heat. In addition, it was also possible to confirm that ice formation actually started at the timing. Thereafter, the temperature was around 0° C. while the certain time passes. Here, the product entered a state where there was a mixture of water and ice. The temperature finally started to decrease again from 0° C. Accordingly, the temperature being measured became a solid temperature within the ice, that is, was not the liquid temperature.

Hereinafter, regarding the conditions A to C, the difference in temperature at this time when the non-cooled surface liquid temperature became a melting point (0° C.), the difference in temperature immediately before the temperature of the shelf is decreased from −10° C. to −20° C., and the difference in temperature immediately before the generation of solidification heat will be described. The "difference in temperature immediately before" referred in the present invention indicates the highest temperature in the difference in temperature which can be detected between 1 second to 20 seconds before an event (such as the generation of solidification heat).

Condition A:

Difference in temperature at this time when non-cooled surface liquid temperature became melting point (0° C.): 1.1° C.

Difference in temperature immediately before temperature is decreased from −10° C. to −20° C.: 0.2° C.

Difference in temperature immediately before generation of solidification heat: 1.1° C.

Condition B:

Difference in temperature at this time when non-cooled surface liquid temperature became melting point (0° C.): 1.0° C.

Difference in temperature immediately before temperature is decreased from −10° C. to −20° C.: 0.1° C.

Difference in temperature immediately before generation of solidification heat: 0.9° C.

Condition C:

Difference in temperature at this time when non-cooled surface liquid temperature became melting point (0° C.): 1.8° C.

Difference in temperature immediately before temperature is decreased from −10° C. to −20° C.: 1.1° C.

Difference in temperature immediately before generation of solidification heat: 2.1° C.

[Reference Example 3] Production of Biocompatible Macromolecular Block (Pulverizing and Cross-Linking of Porous Body)

The CBE3 porous bodies of Condition A and Condition B which had been obtained in Reference Example 2 were pulverized using NEW POWERMILL (Osaka Chemical Co., Ltd., NEW POWERMILL PM-2005). The pulverizing was performed for one minute×5 times, that is, for 5 minutes in total at the maximum rotation speed. The sizes of the obtained pulverized substances were divided using a stainless steel sieve to obtain uncross-linked blocks with 25 to 53 µm, 53 to 106 µm, and 106 to 180 µm. Thereafter, biocompatible macromolecular blocks (CBE3 blocks) were obtained by performing thermal cross-linking (six kinds of cross-linking times of 8 hours, 16 hours, 24 hours, 48 hours, 72 hours, and 96 hours) at 160° C. under reduced pressure.

Hereinafter, a porous body-derived block under the condition A which has been cross-linked for 48 hours is called E, and a porous body-derived block under the condition B which has been cross-linked for 48 hours is called F. E and F are blocks with a small difference in temperature which have been produced from porous bodies produced through a freezing step in which the difference in temperature is small. There was no influence of the difference in cross-linking time on the performance in the evaluation of the present example. Therefore, the blocks cross-linked for 48 hours were representatively used. In addition, there was no difference in performance between E and F. In the following reference examples and examples, biocompatible macromolecular blocks which have sizes of 53 to 106 µm, are produced under the condition A, and of which the cross-linking time is 48 hours were used.

[Reference Example 4] Measurement of Tap Density of Biocompatible Macromolecular Block The tap density is a value indicating how much volume of block can be densely filled. It can be said that, as the value becomes smaller, the block cannot be densely filled, that is, the structure of the block is complicated. The tap density was measured as follows. First, a funnel with an attached cap (having a cylindrical shape with a diameter of 6 mm and a length of 21.8 mm: capacity of 0.616 $cm^3$) at the tip thereof was prepared, and the mass of only the cap was measured. Thereafter, the cap was attached to the funnel, and blocks were poured from the funnel so as to be collected in the cap. After placing a sufficient amount of block, the cap portion was hit 200 times on a hard object such as a desk, the funnel was removed, and the blocks were leveled with a spatula. The mass was measured in a state where the cap was filled up with the blocks. The tap density was obtained by calculating the mass of only the blocks from the difference between the mass of the cap filled up with the blocks and the mass of only the cap, and dividing the mass of only the blocks by the volume of the cap.

As a result, the tap density of the biocompatible macromolecular blocks of Reference Example 3 is 98 mg/$cm^3$.

[Reference Example 5] Measurement of Cross-Linking Degree of Biocompatible Macromolecular Block The cross-linking degree (the number of cross-linking times per molecule) of the blocks cross-linked in Reference Example 3 was calculated. The measurement was performed through a TNBS (2,4,6-trinitrobenzene sulfonic acid) method.

<Preparation of Sample>

A sample (about 10 mg), 4 mass % $NaHCO_3$ aqueous solution (1 mL), and 1 mass % TNBS aqueous solution (2 mL) were added to a glass vial, and the mixture was shaken for 3 hours at 37° C. Thereafter, 37 mass % hydrochloric acid (10 mL) and pure water (5 mL) were added thereto, and then, the mixture was allowed to stand for 16 hours or longer at 37° C. to prepare a sample.

<Preparation of Blank>

A sample (about 10 mg), 4 mass % $NaHCO_3$ aqueous solution (1 mL), and 1 mass % TNBS aqueous solution (2 mL) were added to a glass vial, 37 mass % hydrochloric acid (3 mL) was immediately added thereto, and the mixture was shaken for 3 hours at 37° C. Thereafter, 37 mass % hydrochloric acid (7 mL) and pure water (5 mL) were added thereto, and then, the mixture was allowed to stand for 16 hours or longer at 37° C. to prepare a blank.

The absorbance (wavelength of 345 nm) of the sample and the blank which had been diluted 10 times with pure water was measured, and the cross-linking degree (the number of cross-linking times per molecule) was calculated from (Formula 2) and (Formula 3).

$$(As-Ab)/14{,}600 \times V/w \qquad \text{(Formula 2)}$$

(Formula 2) represents the amount (molar equivalent) of lysine per 1 g of recombinant peptide.

(In the formula, as represents the sample absorbance, Ab represents the blank absorbance, V represents the reaction liquid amount (g), and w represents the mass (mg) of recombinant peptide.)

$$1-(\text{sample (Formula 2)/uncross-linked recombinant peptide (Formula 2)}) \times 34 \qquad \text{(Formula 3)}$$

(Formula 3) represents the number of cross-linking times per molecule.

As a result, the cross-linking degree of the biocompatible macromolecular blocks of Reference Example 3 is 4.2.

[Reference Example 6] Measurement of Water Absorption Rate of Biocompatible Macromolecular Block The water absorption rate of biocompatible macromolecular blocks produced in Reference Example 3 was calculated.

A 3 cm×3 cm nylon mesh bag was filled with about 15 mg of the biocompatible macromolecular blocks at 25° C. and was swollen in ion exchange water for 2 hours. Then, the biocompatible macromolecular blocks were dried with air for 10 minutes, and the mass was measured at each stage to obtain the water absorption rate according to (Formula 4).

Water absorption rate=$(w2-w1-w0)/w0$     (Formula 4)

(In the formula, w0 represents the mass of a material before water absorption, w1 represents the mass of an empty bag after water absorption, and w2 represents the mass of the entirety of the bag containing the material after water absorption.)

As a result, the water absorption rate of the blocks of Reference Example 3 is 786%.

In the following, VPA means valproic acid.

All cell cultures in Comparative Example 1, Reference Example 7, Example 1, and Example 2 described below were performed at 37° C. and 5% $CO_2$.

[Comparative Example 1] Induction of Differentiation of Cells Only (VPA-)

Commercially available human fat-derived mesenchymal stem cells (hADSC: Lonza) were thawed and passaged until 5 passages had passed. As for the number of passages at this stage, the results did not change even after 8 passages.

Thereafter, the cells were seeded at $5\times10^5$ cells/well in 12 wells, and as Step 1, the product was cultured with the following medium and compound for 7 days.
DMEM/F12; Gibco, 1 mass % B27-supplement; Invitrogen, 1 mass % N2-supplement; Invitrogen, 50 ng/mL activin A; Peprotech, 10 nmol/L exendin-4; Sigma, 1 mass % human-Albumin.

In addition, the result did not change even if the culture period at this stage was 9 days.

Thereafter, the obtained cell aggregate was cultured as Step 2 using the following medium for 14 days.
DMEM/F12; Gibco, 1 mass % B27-supplement; Invitrogen, 1 mass % N2-supplement; Invitrogen, 50 ng/mL activin A; Peprotech, 10 nmol/L exendin-4; Sigma, 1 mass % human-Albumin, 10 mmol/L nicotinamide; Sigma, 50 ng/mL hepatocyte growth factor; Peprotech.

In addition, the result did not change even if the period of cultures at this stage was 28 days.

[Reference Example 7] Induction of Differentiation of Cells Only (VPA+)

Commercially available human fat-derived mesenchymal stem cells (hADSC: Lonza) were thawed and passaged until 5 passages had passed. As for the number of passages at this stage, the results did not change even after 8 passages.

Thereafter, the cells were seeded at $5\times10^5$ cells/well in 12 wells, and as Step 1, the product was cultured with the following medium and compound for 7 days.
DMEM/F12; Gibco, 1 mass % B27-supplement; Invitrogen, 1 mass % N2-supplement; Invitrogen, 50 ng/mL activin A; Peprotech, 10 nmol/L exendin-4; Sigma, 1 mass % human-Albumin.

In addition, the result did not change even if the culture period at this stage was 9 days.

Thereafter, the obtained cell aggregate was cultured as Step 2 using the following medium for 14 days.
DMEM/F12; Gibco, 1 mass % B27-supplement; Invitrogen, 1 mass % N2-supplement; Invitrogen, 50 ng/mL activin A; Peprotech, 10 nmol/L exendin-4; Sigma, 1 mass % human-Albumin, 10 mmol/L nicotinamide; Sigma, 50 ng/mL hepatocyte growth factor; Peprotech, 1 mmol/L Valproic acid.

In addition, the result did not change even if the period of cultures at this stage was 28 days.

[Example 1] Induction of Differentiation in Cell Structure (Mosaic Cell Aggregation) (VPA-)

Commercially available human fat-derived mesenchymal stem cells (hADSC: Lonza) were thawed and passaged until 5 passages had passed. As for the number of passages at this stage, the results did not change even after 8 passages.

Thereafter, 0.5 mg of the biocompatible macromolecular block (53-106 pin) prepared in Reference Example 3 were seeded at $5\times10^5$ cells/well in 12 wells, and as Step 1, the product was cultured with the following medium and compound for 7 days.
DMEM/F12; Gibco, 1 mass % B27-supplement; Invitrogen, 1 mass % N2-supplement; Invitrogen, 50 ng/mL activin A; Peprotech, 10 nmol/L exendin-4; Sigma, 1 mass % human-Albumin.

The result did not change even if the culture period at this stage was 9 days.

Thereafter, the obtained cell aggregate was cultured as Step 2 using the following medium for 14 days.
DMEM/F12; Gibco, 1 mass % B27-supplement; Invitrogen, 1 mass % N2-supplement; Invitrogen, 50 ng/mL activin A; Peprotech, 10 nmol/L exendin-4; Sigma, 1 mass % human-Albumin, 10 mmol/L nicotinamide; Sigma, 50 ng/mL hepatocyte growth factor; Peprotech.

The result did not change even if the culture period at this stage was 28 days.

[Example 2] Induction of Differentiation in Cell Structure (Mosaic Cell Aggregation) (VPA+)

Commercially available human fat-derived mesenchymal stem cells (hADSC: Lonza) were thawed and passaged until 5 passages had passed. As for the number of passages at this stage, the results did not change even after 8 passages.

Thereafter, 0.5 mg of the biocompatible macromolecular block (53-106 μm) prepared in Reference Example 3 were seeded at $5\times10^5$ cells/well in 12 wells, and as Step 1, the product was cultured with the following medium and compound for 7 days.
DMEM/F12; Gibco, 1 mass % B27-supplement; Invitrogen, 1 mass % N2-supplement; Invitrogen, 50 ng/mL activin A; Peprotech, 10 nmol/L exendin-4; Sigma, 1 mass % human-Albumin.

The result did not change even if the culture period at this stage was 9 days.

Thereafter, the obtained cell aggregate was cultured as Step 2 using the following medium for 14 days.
MEM/F12; Gibco, 1 mass % B27-supplement; Invitrogen, 1 mass % N2-supplement; Invitrogen, 50 ng/mL activin A; Peprotech, 10 nmol/L exendin-4; Sigma, 1 mass % human-Albumin, 10 mml/L nicotinamide; Sigma, 50 ng/mL hepatocyte growth factor; Peprotech, 1 mmol/L valproic acid.

In addition, the result did not change even if the period of cultures at this stage was 28 days.

[Test Example 1] Evaluation

Figure 4:
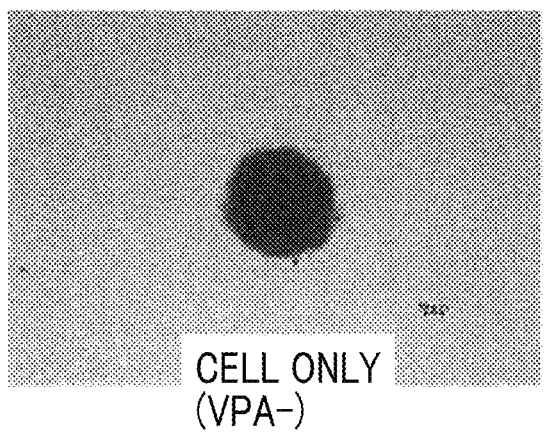
FIG. 4 shows a result of confirmation of insulin-producing cells by dithizone staining.
Figure 4:
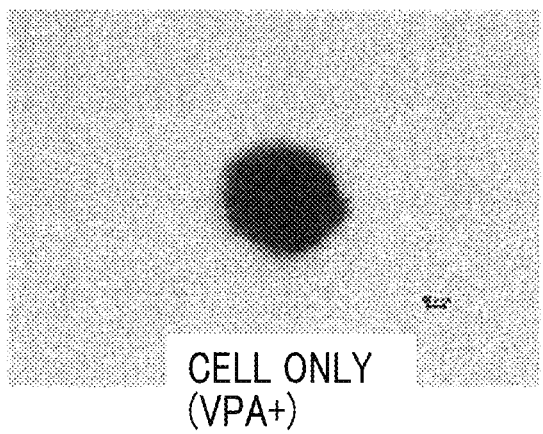
Figure 4:
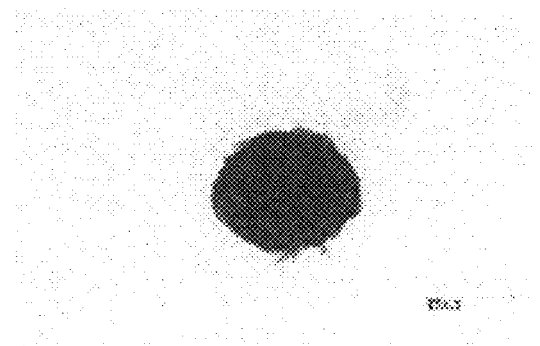
Figure 4:
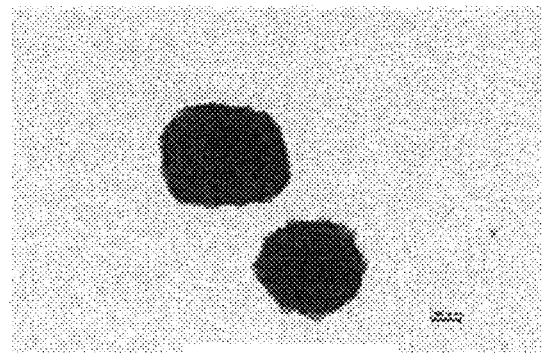

The insulin-producing cells (IPCs) obtained in Comparative Example 1, Reference Example 7, Example 1, and Example 2 were confirmed by dithizone staining at a concentration of 2 µg/ml. As a result, as shown in FIG. 4, the insulin-producing cells obtained in Example 1 and Example 2 were stained red well by dithizone staining, and it was considered that there were many insulin-producing cells. In FIG. 4, only cells (VPA-) indicate Comparative Example 1, only cells (VPA+) indicate Reference Example 7, cell structures (VPA-) indicate Example 1, and cell structures (VPA+) indicate Example 2.

In addition, the insulin secretion ability of each of the obtained IPCs by glucose responsiveness was measured. Using Krebs-Ringer bicarbonate (KRB) buffer as a medium component, the concentration of insulin in the medium when $5 \times 10^5$ cells were cultured at a concentration of 20 mmol/L glucose for 60 minutes in a 2 mL medium volume was measured by enzyme-linked immunosorbent assay (ELISA). In addition, using Krebs-Ringer bicarbonate (KRB) buffer as a medium component, the concentration of insulin in the medium when $5 \times 10^5$ cells were cultured at a concentration of 3 mmol/L glucose for 60 minutes in a 2 mL medium volume was measured by ELISA. The value (ratio) obtained by dividing the "concentration at 20 mmol/L glucose" by the "concentration at 3 mmol/L glucose" was obtained as Stimulation Index (SI).

Figure 5:
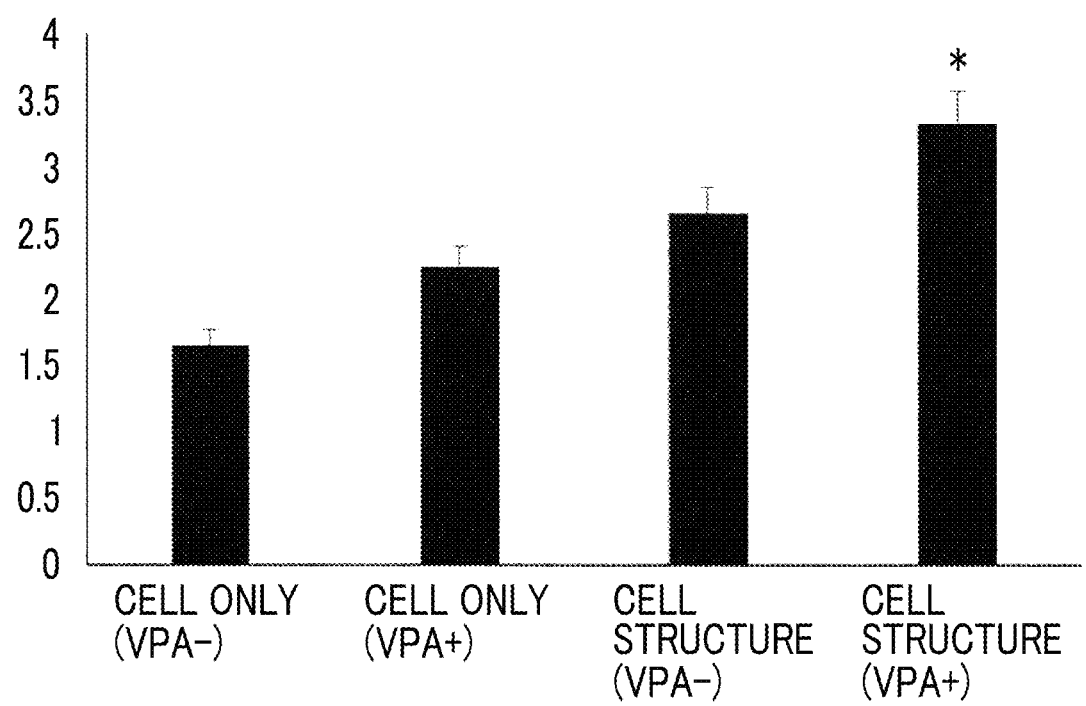
FIG. 5 shows a result of measurement of insulin secretion ability (Stimulation Index: SI) of insulin-producing cells due to glucose responsiveness.

As a result, as shown in FIG. 5, the SI was 1.64 in Comparative Example 1, 2.24 in Reference Example 7, 2.53 in Example 1, and 3.42 in Example 2. This indicates that in a case where differentiation was induced from mesenchymal stem cells into insulin-producing cells using the cell structure, differentiation was induced with high efficiency into the insulin-producing cells, and SI was increased. Furthermore, it was found that in a case where VPA, which is an HDAC inhibitor, was used in combination with the cell structure, SI was significantly improved. In FIG. 5, only cells (VPA-) indicate Comparative Example 1, only cells (VPA+) indicate Reference Example 7, cell structures (VPA-) indicate Example 1, and cell structures (VPA+) indicate Example 2.

Example 3

Figure 6:
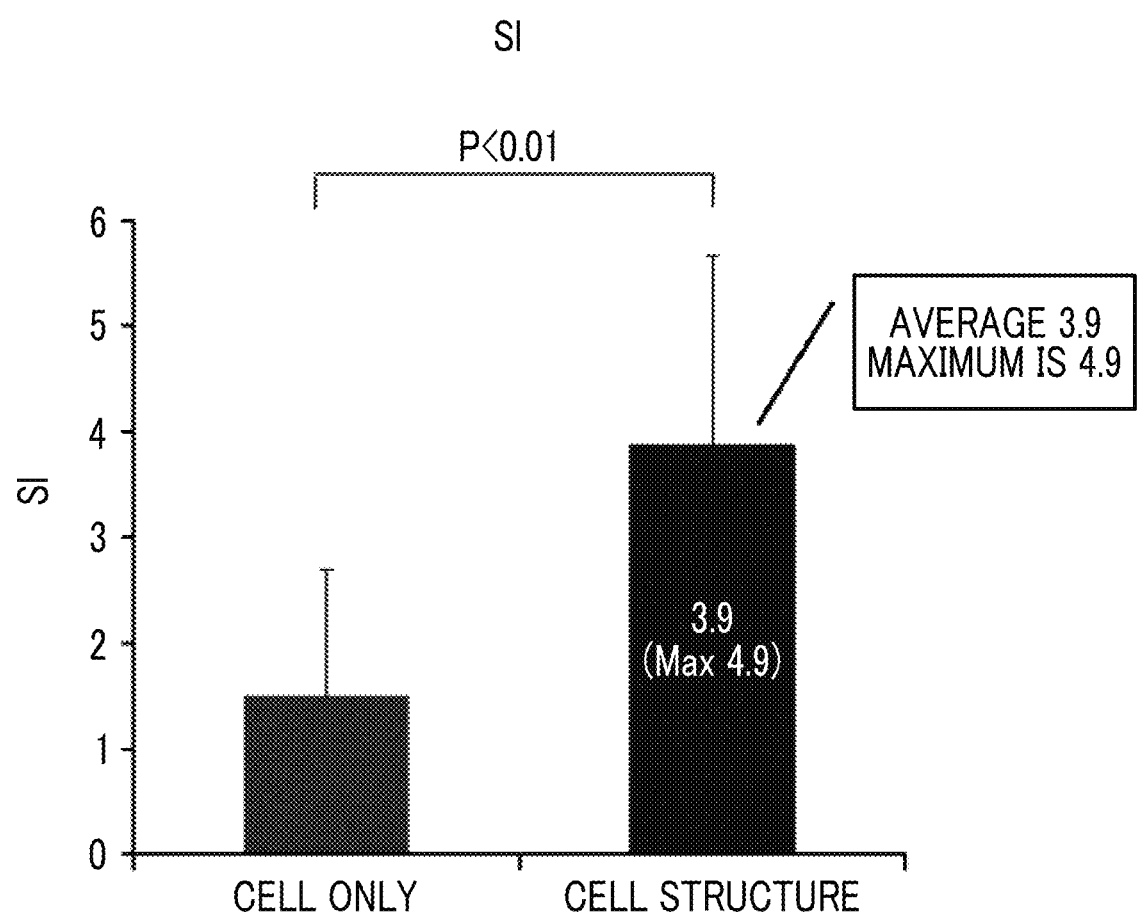
FIG. 6 shows SI repeatability in a cell only and a cell structure.

In addition, for confirmation, an experiment for confirming reproducibility was repeated five times for the results of the cells only and the cell structure. As a result, as shown in FIG. 6, in a case where only cells were used, the SI was about 1.5 on average. On the other hand, in the case of the cell structure, it was confirmed that the SI was 3.9, and a significant difference occurred. In the case of the cell structure, the SI was 4.9 at the maximum. By the way, it is said that the SI is 2.0 or more in a normal living body-derived pancreatic islet.

Example 4

Subsequently, the differentiation-induced cell structure was transplanted into a diabetic model mouse to evaluate whether the blood glucose level could be controlled or not. In addition, the diabetic model mouse was administered to a nude mouse (BALB/cAJcl-nu/nu) at a dose of 200 mg/kg streptozotocin, and an individual whose blood sugar level exceeded 250 mg/dl twice, or an individual whose blood sugar level exceeded 300 mg/dl one time was used as the diabetic model mouse.

Upon transplantation, 150 (150 IE) or 300 (300 IE) of the cell structures of which differentiation was induced prepared in Example 2 were transplanted. The transplantation site was transplanted under the renal capsule. In the evaluation, the blood glucose level was measured.

Figure 7:
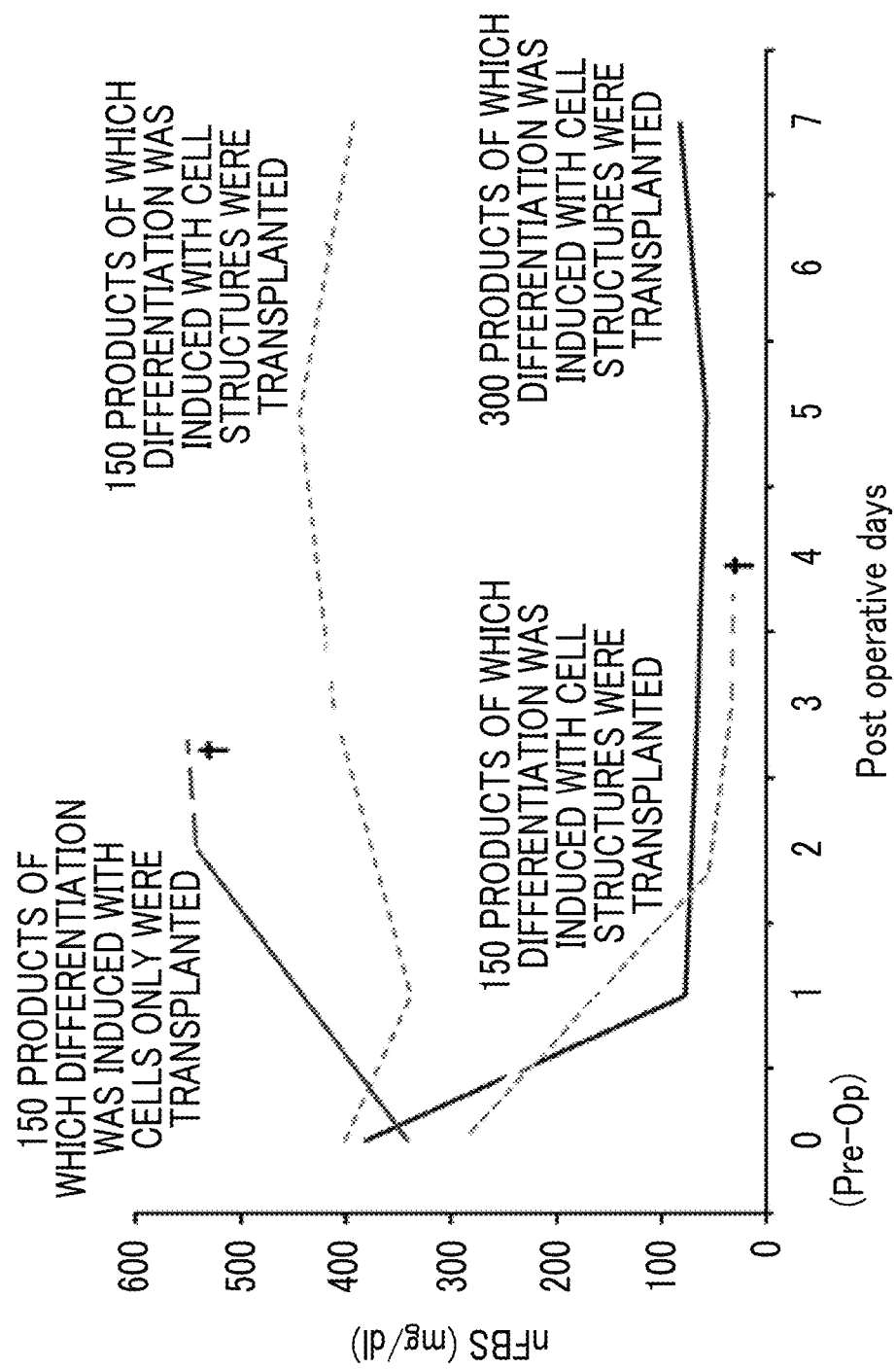
FIG. 7 shows a blood glucose level and the number of transplantation days in a test in which a differentiation-induced cell structure was transplanted into a diabetes model mouse.

As a result, as shown in FIG. 7, in a case where 150 cell structures were transplanted, there were an individual whose blood glucose level after transplantation was within a normal range (200 mg/dl or less) of lower than 200 mg/dl and an individual whose blood glucose level after transplantation remained unchanged at about 400 mg/dl. On the other hand, in a case where 300 cell structures were transplanted, the blood glucose level became 200 mg/dl or less from the first day after transplantation, and the blood glucose level was reliably controlled. For reference, 150 cells were transplanted with the cells only (VPA-) prepared in Reference Example 7. However, after transplantation, it was confirmed that the blood glucose level was not decreased but remained elevated.

Figure 8:
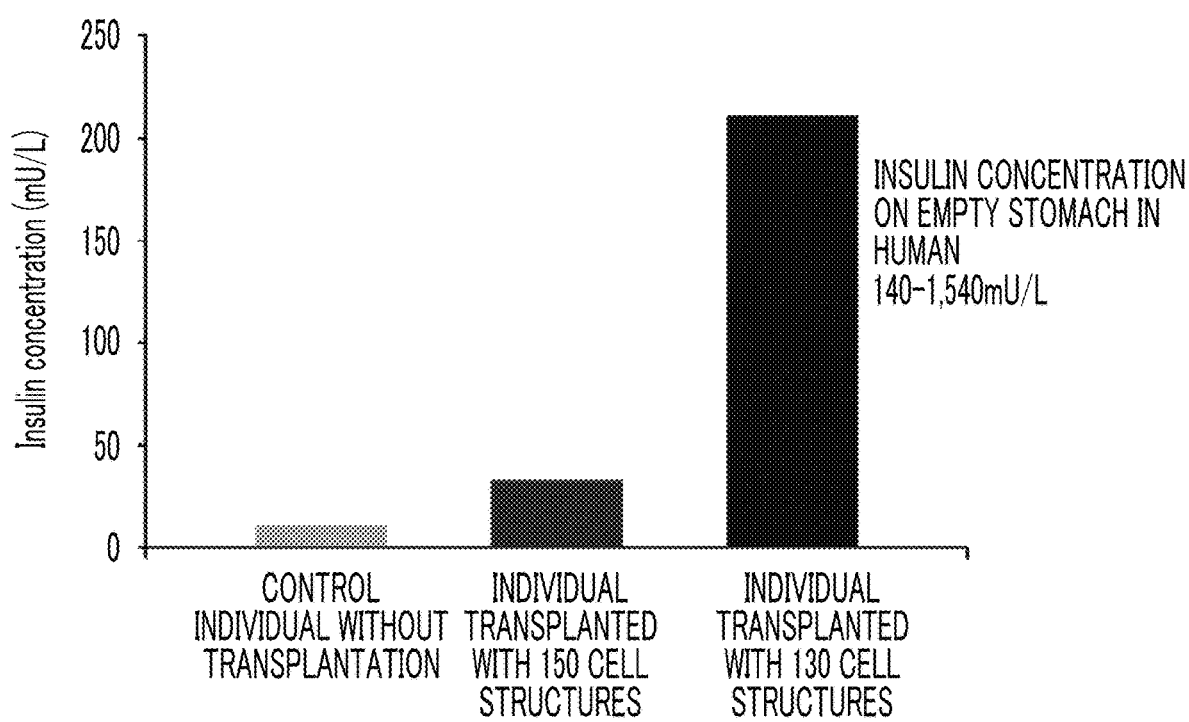
FIG. 8 shows a human insulin concentration in blood in the test in which a differentiation-induced cell structure was transplanted into a diabetes model mouse.

In addition, with respect to 150 individuals transplanted with cell structures of which blood glucose level could not be controlled to 200 mg/dl or less and 300 individuals transplanted with cell structures of which blood glucose level could be controlled to 200 mg/dl or less, whether human insulin was detected or not in the blood of mice was measured by the ELISA method after seven days from the transplantation. As a result, as shown in FIG. 8, almost no human insulin was detected in the control individual without transplantation, and in the individual transplanted with 150 cell structures, a low human insulin concentration of about 30 mU/L was measured in the blood of the mouse. On the other hand, in the individual transplanted with 300 cell structures, the human insulin concentration in the blood of the mouse was detected as a high value exceeding 200 mU/L. In humans, it is said that in a human, the value was 140-1,540 mU/L on an empty stomach in a human, and in a case where 300 cell structures were transplanted, it is found that the human insulin in the range was acknowledged. In addition, crossovers have been found to be less than 0.3% for human insulin and mouse insulin, and it may be considered that high levels of human insulin in blood in an individual transplanted with 300 cell structures is not derived from mice.

From this, it was considered that the differentiation-induced cell structure exhibited an SI of 2 or more, and had an ability to release insulin in the body and control the blood glucose level in animal tests.

SEQUENCE LISTING

PCT_In from mesenchymal stem cells_20181108_120429_0.txt

What is claimed is:

1. A method for producing an insulin-producing cell from a mesenchymal stem cell, the method comprising:
   (a) a step of producing a cell structure which contains a plurality of biocompatible macromolecular blocks and a plurality of mesenchymal stem cells and in which at least one of the biocompatible macromolecular block is arranged in a gap between the plurality of mesenchymal stem cells, by incubating the plurality of biocompatible macromolecular blocks and the plurality of mesenchymal stem cells;
   (b) a step of culturing one or more of the mesenchymal stem cells before the incubation in the step (a), the mesenchymal stem cell in the incubation in the step (a), or the cell structure produced in the step (a) in a medium containing the GLP-1 receptor agonist; and
   (c) a step of culturing the cell structure obtained in the step (a) or the step (b) in a medium containing a water-soluble vitamin and a hepatocyte growth factor to induce differentiation of the mesenchymal stem cells into insulin-producing cells.

2. The method according to claim 1, wherein the step (b) is performed for 3 to 14 days.

3. The method according to claim 1, wherein the step (c) is performed for 7 to 35 days.

4. The method according to claim 1, wherein the GLP-1 receptor agonist is exendin-4.

5. The method according to claim 1, wherein the water-soluble vitamin is nicotinamide.

6. The method according to claim 1, wherein the medium in the step (b) further contains activin A.

7. The method according to claim 1, wherein the medium in the step (c) further contains a histone deacetylation inhibitor.

8. The method according to claim 7, wherein the histone deacetylation inhibitor is a valproic acid.

9. The method according to claim 1, wherein the step (a) and the step (b) are steps of producing a cell structure which contains a plurality of biocompatible macromolecular blocks and a plurality of mesenchymal stem cells and in which at least one of the biocompatible macromolecular blocks is arranged in a gap between the plurality of mesenchymal stem cells, by incubating the plurality of biocompatible macromolecular blocks and the plurality of mesenchymal stem cells in a medium containing a GLP-1 receptor agonist.

10. The method according to claim 1,
wherein the mesenchymal stem cells are fat-derived stem cells.

11. The method according to claim 1,
wherein the biocompatible macromolecular block is formed of a recombinant peptide.

12. The method according to claim 11,
wherein the recombinant peptide is represented by the following formula, Formula: A-[(Gly-X-Y)$_n$]$_m$-B, in the formula, A represents an arbitrary amino acid or an amino acid sequence, B represents an arbitrary amino acid or an amino acid sequence, n pieces of X each independently represent any amino acid, n pieces of Y each independently represent any amino acid, n represents an integer of 3 to 100, and m represents an integer of 2 to 10. Here, n pieces of Gly-X-Y may be the same as or different from each other.

13. The method according to claim 11,
wherein the recombinant peptide is any one of a peptide formed of an amino acid sequence described in SEQ ID NO: 1; a peptide which is formed of an amino acid sequence in which one or several amino acids are deleted, substituted, or added in the amino acid sequence described in SEQ ID NO: 1 and has a biocompatibility; or a peptide which is formed of an amino acid sequence having 85% or more sequence identity to the amino acid sequence described in SEQ ID NO: 1 and has a biocompatibility.

14. The method according to claim 1,
wherein in the biocompatible macromolecular block, a biocompatible macromolecule is cross-linked by heat, ultraviolet rays, or an enzyme.

15. The method according to claim 1,
wherein the biocompatible macromolecular block is in a form of granules obtained by grinding a porous body of biocompatible macromolecules.

* * * * *

SEQUENCE LISTING

<160> NUMBER OF SEQ ID NOS: 11

<210> SEQ ID NO 1
<211> LENGTH: 571

```
<212> TYPE: PRT
<213> ORGANISM: Artificial Sequence
<220> FEATURE:
<223> OTHER INFORMATION: Synthetic: Recombinant

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
            35                  40                  45

Gly Leu Gln Gly Met Pro Gly Glu Arg Gly Ala Ala Gly Leu Pro Gly
        50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
            115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
            260                 265                 270

Asp Gly Val Arg Gly Leu Ala Gly Pro Ile Gly Pro Pro Gly Glu Arg
        275                 280                 285

Gly Ala Ala Gly Leu Pro Gly Pro Lys Gly Glu Arg Gly Asp Ala Gly
    290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Glu Arg Gly Asp Ala Gly Pro Lys Gly Ala Asp Gly Ala
        355                 360                 365

Pro Gly Lys Asp Gly Val Arg Gly Leu Ala Gly Pro Pro Gly Ala Pro
    370                 375                 380
```

-continued

```
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
            420                 425                 430
Gly Glu Arg Gly Ala Ala Gly Leu Pro Gly Pro Lys Gly Glu Arg Gly
        435                 440                 445
Asp Ala Gly Pro Lys Gly Ala Asp Gly Ala Pro Gly Lys Asp Gly Val
    450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
            500                 505                 510
Ile Gly Pro Pro Gly Pro Ala Gly Ala Pro Gly Ala Pro Gly Leu Gln
        515                 520                 525
Gly Met Pro Gly Glu Arg Gly Ala Ala Gly Leu Pro Gly Pro Lys Gly
    530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 4

Pro Asp Ser Gly Arg
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 10
```

Glu Arg Gly Asp
1

<210> SEQ ID NO 11
<211> LENGTH: 571
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(571)
<223> OTHER INFORMATION: Every Xaa can be any naturally occurring
      amino acid

<400> SEQUENCE: 11

Gly Ala Pro Gly Xaa Tyr Gly Xaa Tyr Gly Xaa Tyr Gly Xaa Tyr Gly
1               5                   10                  15

Xaa Tyr Gly Xaa Tyr Gly Xaa Tyr Gly Xaa Tyr Gly Xaa Tyr Gly Xaa
            20                  25                  30

Tyr Gly Xaa Tyr Gly Xaa Tyr Gly Xaa Tyr Gly Xaa Tyr Gly Xaa Tyr
        35                  40                  45

Gly Xaa Tyr Gly Xaa Tyr Gly Xaa Tyr Gly Xaa Tyr Gly Xaa Tyr Gly
    50                  55                  60

Xaa Tyr Gly Xaa Tyr Gly Xaa Tyr Gly Xaa Tyr Gly Xaa Tyr Gly Xaa
65                  70                  75                  80

Tyr Gly Xaa Tyr Gly Xaa Tyr Gly Xaa Tyr Gly Xaa Tyr Gly Xaa Tyr
                85                  90                  95

Gly Xaa Tyr Gly Xaa Tyr Gly Xaa Tyr Gly Xaa Tyr Gly Xaa Tyr Gly
            100                 105                 110

Xaa Tyr Gly Xaa Tyr Gly Xaa Tyr Gly Xaa Tyr Gly Xaa Tyr Gly Xaa
        115                 120                 125

Tyr Gly Xaa Tyr Gly Xaa Tyr Gly Xaa Tyr Gly Xaa Tyr Gly Xaa Tyr
    130                 135                 140

Gly Xaa Tyr Gly Xaa Tyr Gly Xaa Tyr Gly Xaa Tyr Gly Xaa Tyr Gly
145                 150                 155                 160

Xaa Tyr Gly Xaa Tyr Gly Xaa Tyr Gly Xaa Tyr Gly Xaa Tyr Gly Xaa
                165                 170                 175

Tyr Gly Xaa Tyr Gly Xaa Tyr Gly Xaa Tyr Gly Xaa Tyr Gly Xaa Tyr
            180                 185                 190

Gly Xaa Tyr Gly Xaa Tyr Gly Xaa Tyr Gly Xaa Tyr Gly Xaa Tyr Gly
        195                 200                 205

Xaa Tyr Gly Xaa Tyr Gly Xaa Tyr Gly Xaa Tyr Gly Xaa Tyr Gly Xaa
    210                 215                 220

Tyr Gly Xaa Tyr Gly Xaa Tyr Gly Xaa Tyr Gly Xaa Tyr Gly Xaa Tyr
225                 230                 235                 240

Gly Xaa Tyr Gly Xaa Tyr Gly Xaa Tyr Gly Xaa Tyr Gly Xaa Tyr Gly
                245                 250                 255

Xaa Tyr Gly Xaa Tyr Gly Xaa Tyr Gly Xaa Tyr Gly Xaa Tyr Gly Xaa
            260                 265                 270

Tyr Gly Xaa Tyr Gly Xaa Tyr Gly Xaa Tyr Gly Xaa Tyr Gly Xaa Tyr
        275                 280                 285

Gly Xaa Tyr Gly Xaa Tyr Gly Xaa Tyr Gly Xaa Tyr Gly Xaa Tyr Gly
    290                 295                 300

Xaa Tyr Gly Xaa Tyr Gly Xaa Tyr Gly Xaa Tyr Gly Xaa Tyr Gly Xaa
305                 310                 315                 320

```
Tyr Gly Xaa Tyr Gly Xaa Tyr Gly Xaa Tyr Gly Xaa Tyr
            325                 330                 335
Gly Xaa Tyr Gly Xaa Tyr Gly Xaa Tyr Gly Xaa Tyr Gly
        340                 345                 350
Xaa Tyr Gly Xaa Tyr Gly Xaa Tyr Gly Xaa Tyr Gly Xaa
            355                 360                 365
Tyr Gly Xaa Tyr Gly Xaa Tyr Gly Xaa Tyr Gly Xaa Tyr
        370                 375                 380
Gly Xaa Tyr Gly Xaa Tyr Gly Xaa Tyr Gly Xaa Tyr Gly
385                 390                 395                 400
Xaa Tyr Gly Xaa Tyr Gly Xaa Tyr Gly Xaa Tyr Gly Xaa
            405                 410                 415
Tyr Gly Xaa Tyr Gly Xaa Tyr Gly Xaa Tyr Gly Xaa Tyr
            420                 425                 430
Gly Xaa Tyr Gly Xaa Tyr Gly Xaa Tyr Gly Xaa Tyr Gly
            435                 440                 445
Xaa Tyr Gly Xaa Tyr Gly Xaa Tyr Gly Xaa Tyr Gly Xaa
        450                 455                 460
Tyr Gly Xaa Tyr Gly Xaa Tyr Gly Xaa Tyr Gly Xaa Tyr
465                 470                 475                 480
Gly Xaa Tyr Gly Xaa Tyr Gly Xaa Tyr Gly Xaa Tyr Gly
            485                 490                 495
Xaa Tyr Gly Xaa Tyr Gly Xaa Tyr Gly Xaa Tyr Gly Xaa
            500                 505                 510
Tyr Gly Xaa Tyr Gly Xaa Tyr Gly Xaa Tyr Gly Xaa Tyr
        515                 520                 525
Gly Xaa Tyr Gly Xaa Tyr Gly Xaa Tyr Gly Xaa Tyr Gly
        530                 535                 540
Xaa Tyr Gly Xaa Tyr Gly Xaa Tyr Gly Xaa Tyr Gly Xaa
545                 550                 555                 560
Tyr Gly Xaa Tyr Gly Xaa Tyr Gly Xaa Tyr Gly
            565                 570
```